(12) United States Patent
Toguchida et al.

(10) Patent No.: US 9,921,212 B2
(45) Date of Patent: Mar. 20, 2018

(54) PREVENTIVE AND THERAPEUTIC DRUG FOR CARTILAGINOUS HYPERPLASIA AND METHOD OF SCREENING FOR THE SAME

(71) Applicant: KYOTO UNIVERSITY, Kyoto (JP)

(72) Inventors: Junya Toguchida, Kyoto (JP); Ryuta Nishikomori, Kyoto (JP); Koji Yokoyama, Kyoto (JP); Makoto Ikeya, Kyoto (JP); Toshio Heike, Kyoto (JP)

(73) Assignee: Kyoto University, Kyoto (JP)

( * ) Notice: Subject to any disclaimer, the term of this patent is extended or adjusted under 35 U.S.C. 154(b) by 9 days.

(21) Appl. No.: 14/879,507

(22) Filed: Oct. 9, 2015

(65) Prior Publication Data
US 2016/0177406 A1 Jun. 23, 2016

(30) Foreign Application Priority Data

Nov. 7, 2014 (JP) ................. 2014-227500

(51) Int. Cl.
*G01N 33/50* (2006.01)
*C07D 473/34* (2006.01)

(52) U.S. Cl.
CPC ....... *G01N 33/5041* (2013.01); *C07D 473/34* (2013.01); *G01N 33/5038* (2013.01); *G01N 33/5044* (2013.01); *G01N 2333/4703* (2013.01); *G01N 2400/00* (2013.01); *G01N 2400/40* (2013.01); *G01N 2440/14* (2013.01); *G01N 2500/10* (2013.01)

(58) Field of Classification Search
None
See application file for complete search history.

(56) References Cited

U.S. PATENT DOCUMENTS

2002/0061514 A1* 5/2002 Underhill ............. C12Q 1/6897
435/4
2009/0068742 A1 3/2009 Yamanaka

FOREIGN PATENT DOCUMENTS

WO WO 2007/069666 A1 6/2007

OTHER PUBLICATIONS

Choi et al. European Journal of Pharmacology. 2011. 655:9-15.*
Yokoyama et al., "Enhanced chondrogenesis of iPS cells from neonatal-onset multisystem inflammatory disease occurs via the caspase-1 independent cAMP/PKA/CREB pathway," Arthritis Rheumatol., Oct. 9, 2014, doi: 10.1002/art.38912, 39 pages.
Aróstegui et al., "A Somatic NLRP3 Mutation as a Cause of a Sporadic Case of Chronic Infantile Neurologic, Cutaneous, Articular Syndrome/Neonatal-Onset Multisystem Inflammatory Disease," Arthritis & Rheumatism, Apr. 2010, 62(4):1158-1166.
Bauernfeind et al., "Cutting Edge: NF-κB Activating Pattern Recognition and Cytokine Receptors License NLRP3 Inflammasome Activation by Regulating NLRP3 Expression," The Journal of Immunology, 2009, 183(2):787-791.
Gattorno et al., "Beyond the NLRP3 Inflammasome," Arthritis & Rheumatism, May 2013, 65(5):1137-1147.
Hoffman et al., "Mutation of a new gene encoding a putative pyrin-like protein causes familial cold autoinflammatory syndrome and Muckle-Wells syndrome," Nature Genetics, Nov. 2001 (online Oct. 22, 2001), 29(3):301-305.
Latz et al., "Activation and regulation of the inflammasomes," Nature Reviews Immunology, Jun. 2013, 13(6):397-411.
Mariathasan et al., "Cryopyrin activates the inflammasome in response to toxins and ATP," Nature, Mar. 9, 2006, 440(7081):228-232.
Takahashi et al., "Induction of Pluripotent Stem Cells from Adult Human Fibroblasts by Defined Factors," Cell, Nov. 30, 2007, 131:861-872.
Tanaka et al., "Induced pluripotent stem cells from CINCA syndrome patients as a model for dissecting somatic mosaicism and drug discovery," Blood, Aug. 9, 2012 (online Jun. 21, 2012), 120(6):1299-1308.
Tanaka et al., "High Incidence of NLRP3 Somatic Mosiacism in Patients With Chronic Infantile Neurologic, Cutaneous, Articular Syndrome: Results of an International Multicenter Collaborative Study," Arthritis Rheum., Nov. 2011, 63(11):3625-3632.

* cited by examiner

Primary Examiner — Joseph G. Dauner
(74) Attorney, Agent, or Firm — Foley & Lardner LLP

(57) ABSTRACT

A method of screening for a therapeutic and/or preventive drug for cartilaginous hyperplasia and a therapeutic and/or preventive drug for cartilaginous hyperplasia are provided.

The following are provided: a method of screening for a therapeutic and/or preventive drug for cartilaginous hyperplasia, comprising a step of culturing chondroprogenitor cells under conditions in which the cells are brought into contact with a test substance and conditions in which the cells are not brought into contact with the test substance and a step of determining the SOX9 promoter activity, cAMP level, or degree of phosphorylation of CREB in the cells or the extracellular matrix volume in a culture; and a therapeutic and/or preventive drug for cartilaginous hyperplasia, comprising as an active ingredient an adenylate cyclase inhibitor.

4 Claims, 11 Drawing Sheets
(5 of 11 Drawing Sheet(s) Filed in Color)

C.

PREVENTIVE AND THERAPEUTIC DRUG FOR CARTILAGINOUS HYPERPLASIA AND METHOD OF SCREENING FOR THE SAME

CROSS-REFERENCE TO RELATED APPLICATIONS

This application claims priority from Japanese application JP 2014-227500, filed Nov. 7, 2014.

The instant application contains a Sequence Listing which has been submitted in ASCII format via EFS-WEB and is hereby incorporated by reference in its entirety. Said ASCII copy, created on Dec. 22, 2015, is named sequence.txt and is 5 KB.

TECHNICAL FIELD

The present invention relates to a method of screening for a preventive and/or therapeutic drug for cartilaginous hyperplasia. The present invention also relates to a therapeutic drug for cartilaginous hyperplasia.

BACKGROUND ART

Systemic autoimmune disorder is a disease that is classified as a form of primary immunodeficient syndrome, which is caused by a deficiency in the innate immune system (and especially a deficiency involving pattern-recognition receptors) and is characterized by exhibiting an uncontrollable immune response. Neonatal onset multisystem inflammatory disease (NOMID) is a disease belonging to a group of such systemic autoimmune disorders, and the NLRP3 gene has been identified as the cause of NOMID (Non-Patent Document 1). Clinical findings regarding NOMID include many pathological conditions characterized by neonatal onset chronic inflammation, urticarial rash, and epiphyseal hyperplasia of long bones (Non-Patent Document 2).

Regarding physiological functions of the NLRP3 gene, when the gene is activated by a ligand, a protein complex called "NLRP3 inflammasome" which comprises a plurality of proteins is formed to activate capase-1, cleave pro IL-1β, and eventually activate IL-1β (Non-Patent Documents 3 to 6). Previously attempted therapies for NOMID patients include an anti-IL-1β therapy targeting IL-1β. Although such therapy is effective in suppressing systemic inflammation, it is not sufficiently effective against pathological conditions such as epiphyseal hyperplasia of long bones (Non-Patent Document 7). Therefore, the development of a novel therapy from a different perspective regarding the pathological conditions of NOMID has been awaited.

Meanwhile, in the field of regenerative medicine or the like, technology for converting cells that are useful as biomaterial into cells of a desired cell type has been anticipated. Recently, mouse and human induced pluripotent stem cells (iPS cells) have been established. Yamanaka et al. succeeded in establishing iPS cells by introducing four genes (namely, Oct3/4, Sox2, Klf4, and c-Myc) into human-skin-derived fibroblasts (Patent Document 1 and Non-Patent Document 8). iPS cells that are obtained in the above manner are produced using cells from patients to be treated, thereby allowing them to differentiate into cells of an arbitrary organ. Therefore, iPS cells are considered to enable in vitro reproduction of pathological conditions. Hitherto, successful production of iPS cells from NOMID patients has been reported (Non-Patent Document 9). However, there have been no reports on successful in vitro reproduction of the pathological conditions of NOMID.

PRIOR ART DOCUMENTS

Patent Documents

Patent Document 1: WO2007/069666

Non-Patent Documents

Non-Patent Document 1: Hoffman H M, et al., Nature Genetics. 29(3): 301-305 (2001)
Non-Patent Document 2: Tanaka N, et al., Arthritis and Rheumatism. 63(11): 3625-3632 (2011)
Non-Patent Document 3: Latz E, et al., Nature Reviews Immunology. 13(6): 397-411 (2013)
Non-Patent Document 4: Gattorno M, et al., Arthritis and Rheumatism. 65(5): 1137-1147 (2013)
Non-Patent Document 5: Bauernfeind F G, et al., Journal of Immunology. 183(2): 787-791 (2009)
Non-Patent Document 6: Mariathasan S, et al., Nature. 440(7081): 228-32 (2006)
Non-Patent Document 7: Arostegui J I, et al., Arthritis and Rheumatism. 62(4): 1158-1166 (2010)
Non-Patent Document 8: Takahashi, K, et al., Cell. 131: 861-872 (2007)
Non-Patent Document 9: Tanaka, T, et al., Blood. 9; 120(6): 1299-1308 (2012)

SUMMARY OF INVENTION

Problem to be Solved by the Invention

An object of the present invention is to provide a method of screening for a preventive and/or therapeutic drug for cartilaginous hyperplasia. Another object of the present invention is to provide a therapeutic drug for cartilaginous hyperplasia.

Means for Solving the Problem

As a result of intensive studies that have been undertaken to achieve the above objects, the present inventors succeeded in reproducing pathological conditions of cartilaginous hyperplasia by inducing iPS cells from somatic cells of cartilaginous hyperplasia patients to differentiate into chondrocytes. Specifically, it was found that iPS cells from somatic cells of cartilaginous hyperplasia patients tend to result in the excessive formation of cartilage tissue upon cartilage induction, compared with iPS cells from healthy individuals. Further, as a result of investigation of the cause for hyperplasia of cartilage tissue, it was found that the cause for hyperplasia of cartilage tissue is excessive production of an extracellular matrix from chondrocytes but not increased proliferation of chondroprogenitor cells. Furthermore, as a result of attempts to elucidate the pathological mechanism using chondrocytes induced from iPS cells from somatic cells of cartilaginous hyperplasia patients in order to discover a preventive and/or therapeutic drug for cartilaginous hyperplasia, it was found that the AMP/PKA/CREB signal transduction pathway is involved in hyperplasia of cartilage tissue. It was also found that hyperplasia of cartilage tissue can be suppressed using an adenylate cyclase inhibitor, which is a drug that inhibits the AMP/PKA/CREB signal transduction pathway. The present invention has been completed based on the above findings.

Specifically, the following are provided according to the present invention.

[1] A therapeutic and/or preventive drug for cartilaginous hyperplasia, comprising, as an active ingredient, an adenylate cyclase inhibitor.

[2] The drug of [1], wherein the adenylate cyclase inhibitor is SQ22536.

[3] The drug of [1] or [2], wherein cartilaginous hyperplasia is chronic infantile neurological cutaneous and articular syndrome.

[4] A method of treating and/or preventing cartilaginous hyperplasia, comprising administering an adenylate cyclase inhibitor.

[5] The method of [4], wherein the adenylate cyclase inhibitor is SQ22536.

[6] The method of [4] or [5], wherein cartilaginous hyperplasia is chronic infantile neurological cutaneous and articular syndrome.

[7] Use of an adenylate cyclase inhibitor for production of a therapeutic and/or preventive drug for cartilaginous hyperplasia.

[8] The use of [7], wherein the adenylate cyclase inhibitor is SQ22536.

[9] The use of [7] or [8], wherein cartilaginous hyperplasia is chronic infantile neurological cutaneous and articular syndrome.

[10] An adenylate cyclase inhibitor, which is used for treating and/or preventing cartilaginous hyperplasia.

[11] The inhibitor of [10], wherein the adenylate cyclase inhibitor is SQ22536.

[12] The inhibitor of [10] or [11], wherein cartilaginous hyperplasia is chronic infantile neurological cutaneous and articular syndrome.

[13] A method of screening for a therapeutic and/or preventive drug for cartilaginous hyperplasia, comprising the following steps of:
(a) culturing chondroprogenitor cells under conditions in which the cells are brought into contact with a test substance and conditions in which the cells are not brought into contact with the test substance;
(b) determining promoter activity of SOX9 in the cells obtained in step (a); and
(c) if the promoter activity of SOX9 is lower under conditions in which the cells are brought into contact with a test substance than under conditions in which the cells are not brought into contact with the test substance, selecting the test substance as a therapeutic drug or preventive drug for cartilaginous hyperplasia.

[14] The method of [13], wherein the step of determining promoter activity of SOX9 is a step of determining the amount of mRNA of SOX9.

[15] A method of screening for a therapeutic and/or preventive drug for cartilaginous hyperplasia, comprising the following steps of:
(a) culturing chondroprogenitor cells under conditions in which the cells are brought into contact with a test substance and conditions in which the cells are not brought into contact with the test substance;
(b) determining the cAMP level in the cells obtained in step (a); and
(c) if the cAMP level is lower under conditions in which the cells are brought into contact with a test substance than under conditions in which the cells are not brought into contact with the test substance, selecting the test substance as a therapeutic drug or preventive drug for cartilaginous hyperplasia.

[16] A method of screening for a therapeutic and/or preventive drug for cartilaginous hyperplasia, comprising the following steps of:
(a) culturing chondroprogenitor cells under conditions in which the cells are brought into contact with a test substance and conditions in which the cells are not brought into contact with the test substance;
(b) measuring phosphorylation of CREB in the cells obtained in step (a); and
(c) if the degree of CREB phosphorylation is lower under conditions in which the cells are brought into contact with a test substance than under conditions in which the cells are not brought into contact with the test substance, selecting the test substance as a therapeutic drug or preventive drug for cartilaginous hyperplasia.

[17] The method of any one of [13] to [16], wherein the chondroprogenitor cells are chondroprogenitor cells induced from iPS cells having a mutation in NLRP3.

[18] A method of screening for a therapeutic and/or preventive drug for cartilaginous hyperplasia, comprising the following steps of:
(a) culturing chondroprogenitor cells having an NLRP3 mutation under conditions in which the cells are brought into contact with a test substance and conditions in which the cells are not brought into contact with the test substance;
(b) determining the extracellular matrix volume in a culture obtained in step (a); and
(c) if the extracellular matrix volume is lower under conditions in which the cells are brought into contact with a test substance than under conditions in which the cells are not brought into contact with the test substance, selecting the test substance as a therapeutic drug or preventive drug for cartilaginous hyperplasia.

[19] The method of [18], wherein the extracellular matrix is composed of glycosaminoglycan (GAG).

[20] The method of any one of [17] to [19], wherein the NLRP3 mutation is a Tyr570Cys or Gly307Ser mutation in NLRP3.

[21] The method of any one of [13] to [20], wherein cartilaginous hyperplasia is chronic infantile neurological cutaneous and articular syndrome.

The present specification incorporates the contents of the disclosure of Japanese Patent Application No. 2014-227500 (filed on Nov. 7, 2014) based on which the priority of the present application is claimed.

Effects of Invention

According to the present invention, screening for a preventive and/or therapeutic drug for cartilaginous hyperplasia with the use of a novel tool becomes possible. In addition, the present invention enables the provision of a preventive and/or therapeutic drug for cartilaginous hyperplasia obtained through such screening.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1A shows a summary of culture conditions in a step of differentiation from iPS cells into chondrocytes. FIG. 1B shows Alcian blue staining images and COL2 immunostaining images of chondrocytes differentiated from wild-type NLRP3 iPS cells (lower images) and chondrocytes differentiated from mutant-type NLRP3 iPS cells (upper images). The images are an Alcian blue staining image of 2D micromass culture (2D), an Alcian blue staining image of 3D pellet culture (3D), an enlarged image of 3D Alcian blue staining, a 3D COL2 immunostaining image, and an enlarged image of 3D COL2 immunostaining from the left. FIG. 1C shows quantitative analysis results for the size of a pellet containing wild-type chondrocytes and the size of a pellet containing mutant-type chondrocytes; each pellet was obtained through differentiation induction via 2D micromass culture (the left diagram) or 3D pellet culture (the right diagram).

FIG. 2A shows results of the expression of the chondrocyte-specific genes in the case of two-dimensional micromass culture (2D). FIG. 2B shows results of the expression of the chondrocyte-specific genes in the case of three-dimensional pellet culture (3D).

FIG. 3A shows growth curves of wild-type iPSC- and mutant-type iPSC-derived chondroprogenitor cells. FIG. 3B shows the extracellular matrix volume of cartilage tissue induced via 2D culture. The charts in FIG. 3B show the amount of DNA, total glycosaminoglycan (GAG) level, and level of total GAG per DNA from the left. FIG. 3C shows the extracellular matrix volume of cartilage tissue induced via 3D culture. The charts in FIG. 3C show the amount of DNA, total GAG level, and level of total GAG per DNA from the left.

FIG. 4A shows the expression levels of SOX9 (the left chart), COL2A1 (the center chart), and ACAN (the right chart) in cells on different days after differentiation induction. FIG. 4B shows the expression level of NLRP3 in cells on different days after differentiation induction.

FIG. 5A shows 3D pellet images of cartilaginous pellets from mutant-type iPS cells (the upper images) and wild-type iPS cells (the lower images) that were implanted into immunodeficient mice. The images are macroscopically observed images, Hematoxylin-eosin (HE) staining images, Alcian Blue staining images, and von Koss staining images from the left. FIG. 5B shows quantitative analysis results of the pellet size upon implantation (day 38) and recovery of pellets (day 66).

FIG. 6A shows Alcian blue staining images of induced cartilage tissue obtained after induction with the addition of Ac-YVAD or without the addition of Ac-YVAD (DMSO). FIG. 6B shows results of determining the pellet size of cartilage tissue obtained after induction with the addition of Ac-YVAD or without the addition of Ac-YVAD (DMSO). FIG. 6C shows results of determining the SOX9 expression level of induced chondrocytes obtained after induction with the addition of Ac-YVAD or without the addition of Ac-YVAD (DMSO). FIG. 6D shows the amount of DNA (the left chart), total glycosaminoglycan (GAG) level (the center chart), and level of total GAG per DNA (the right chart) for pellets of induced cartilage tissue obtained after induction with the addition of Ac-YVAD or without the addition of Ac-YVAD (DMSO). FIG. 6E shows Alcian blue staining images of induced cartilage tissue obtained after induction with the addition of IL1-Ra or without the addition of IL1-Ra (PBS/BSA). FIG. 6F shows results of determining the pellet size of induced cartilage tissue obtained after induction with the addition of IL1-Ra or without the addition of IL1-Ra (PBS/BSA). FIG. 6G shows results of determining the SOX9 expression level of induced chondrocytes obtained after induction with the addition of IL1-Ra or without the addition of IL1-Ra (PBS/BSA). FIG. 6H shows the amount of DNA (the left chart), total glycosaminoglycan (GAG) level (the center chart), and level of total GAG per DNA (the right chart) for pellets of induced cartilage tissue obtained after induction with the addition of IL1-Ra or without the addition of IL1-Ra (PBS/BSA).

FIG. 7A is a schematic view of a luciferase reporter construct including an Sox9 proximal promoter (−927/+84 bp). FIG. 7B shows analysis results of human Sox9 promoter activity in wild-type chondroprogenitor cells and mutant-type chondroprogenitor cells. FIG. 7C shows results of determining human Sox9 promoter activity in wild-type chondroprogenitor cells and mutant-type chondroprogenitor cells each having a mutation in its transcription factor binding site. FIG. 7D shows results of determining human Sox9 promoter activity in wild-type chondroprogenitor cells and mutant-type chondroprogenitor cells treated with an adenylate cyclase agonist (forskolin) and an adenylate cyclase antagonist (SQ22536).

EMBODIMENTS FOR CARRYING OUT THE INVENTION

Figure 1:
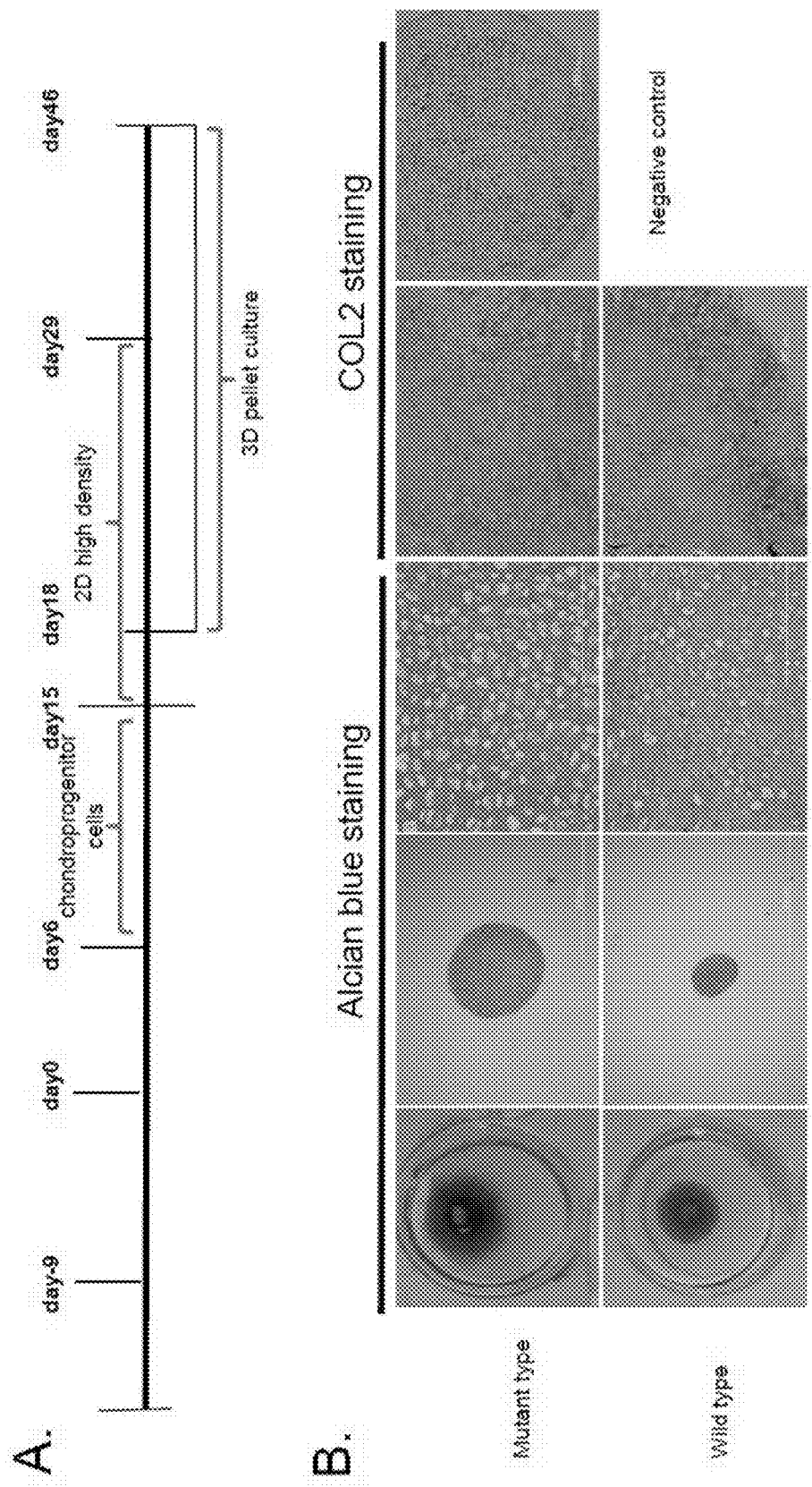
FIGS. 1A to 1C show differentiation of iPS cells from NOMID patients into chondrocytes.
Figure 1:
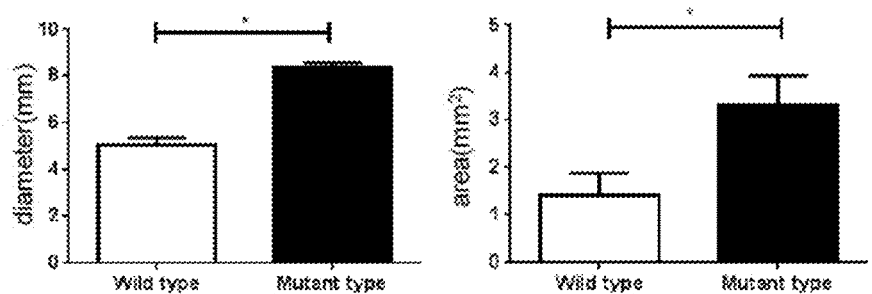

The term "cartilaginous hyperplasia" used herein refers to any bone formation disease resulting from excessive cartilage tissue formation. Examples of cartilaginous hyperplasia include, but are not limited to, cryopyrin-associated periodic syndrome and cartilage-forming tumors such as neonatal onset multisystem inflammatory disease (NOMID), onset multisystem inflammatory disease/chronic infantile neurological cutaneous articular syndrome (OMID/CINCA), familial cold autoinflammatory syndrome, and Muckle-Wells syndrome. Examples of cartilage-forming tumors include, but are not limited to, chondroma (enchondroma or periosteal chondroma), osteochondroma, chondroblastoma, chondromyxoid fibroma, cartilaginous tumors of borderline malignancy, chondrosarcoma, periosteal chodrosarcoma, mesenchymal chondrosarcoma, dedifferentiated chondrosarcoma, clear-cell chondrosarcoma, and malignant chondroblastoma. Preferably, cartilaginous hyperplasia, which is a target disease of the present invention, has pathological conditions such as increased CREB phosphorylation in some chondrocytes. For example, cartilaginous hyperplasia can be chronic infantile neurological cutaneous and articular syndrome. Cartilaginous hyperplasia associated with increased CREB phosphorylation may be observed with a mutation in the causative gene of the disease. For example, such gene with a mutation can be NLRP3. A mutation in NLRP3 may be a gain-of-function or loss-of-function mutation; however, it is preferably a gain-of-function mutation. Preferably, a mutation in NLRP3 can be a Tyr570Cys or Gly307Ser mutation.

A combination of the term "neonatal onset multisystem inflammatory disease" and its abbreviation "NOMID" and a combination of the term "chronic infantile neurological cutaneous and articular syndrome" and its abbreviation "CINCA" used herein each refer to the corresponding identical disease. Therefore, such terms and their abbreviations are interchangeable unless otherwise specified.

<Preventive and/or Therapeutic Drug for Cartilaginous Hyperplasia>

In the present invention, a therapeutic and/or preventive drug for cartilaginous hyperplasia that contains a compound capable of inhibiting the AMP/PKA/CREB signal transduction pathway is provided. Examples of a compound capable of inhibiting the AMP/PKA/CREB signal transduction pathway include protein kinase A (PKA) inhibitors and adenylate cyclase inhibitors. In the present invention, a therapeutic and/or preventive drug for cartilaginous hyperplasia is preferably an adenylate cyclase inhibitor.

In the present invention, a protein kinase A (PKA) inhibitor is not particularly limited as long as PKA is a compound capable of suppressing phosphorylation of CREB (cAMP response element binding protein). Examples thereof include: 4-Cyano-3-methylisoquinoline; Adenosine 3',5'-cyclic Monophosphorothioate, 2'-O-Monobutyryl-, Rp-Isomer, Sodium Salt; Adenosine 3',5'-cyclic Monophosphorothioate, 8-Bromo-, Rp-Isomer, Sodium Salt; Adenosine 3',5'-cyclic Monophosphorothioate, 8-Chloro-, Rp-Isomer, Sodium Salt; Adenosine 3',5'-cyclic Monophosphorothioate, Rp-Isomer, Triethylammonium Salt; Ellagic Acid, Dihydrate; H-7, Dihydrochloride; H-89, Dihydrochloride; H-8, Dihydrochloride; and HA 1004, Dihydrochloride. These compounds can be purchased from Merck Millipore and the like.

In the present invention, an adenylate cyclase inhibitor is not particularly limited as long as it is a compound capable of suppressing adenylate cyclase activity. Therefore, a compound that acts on the intracellular or extracellular signal transduction pathway is included as an adenylate cyclase inhibitor of the present invention as long as it can eventually suppress adenylate cyclase activity. Examples of the adenylate cyclase inhibitor of the present invention include, but are not limited to, SQ22536 (9-(tetrahydro-2-furanyl)-adenine), 2',5'-dideoxyadenosine, 9-cyclopentyladenine, 2',5'-dideoxyadenosine 3'-diphosphate, 2',5'-dideoxyadenosine 3'-monophosphate, MDL-12330A (cis-N-(2-phenylcyclopentyl)azacyclotridece-1-en-2-amine), compounds such as 7,8-dihydro-5(6H)-quinazolinone derivatives disclosed in JP Patent Application No. 2001-153954 (preferably, 2-amino-7-(4-chlorophenyl)-7,8-dihydro-5 (6H)-quinazolinone, 2-amino-7-(4-methoxyphenyl)-7,8-dihydro-5(6H)-quinazolinone, 2-amino-7-phenyl-7,8-dihydro-5(6H)-quinazolinone, 4.2-amino-7-(2-furanyl)-7,8-dihydro-5(6H)-quinazolinone, and 2-amino-7-(2-thienyl)-7,8-dihydro-5 (6H)-quinazolinone), adrenocorticotropic hormone (ACTH), and peptides such as brain natriuretic peptide (BNP) and pituitary adenylate cyclase-activating polypeptide (PACAP). Preferably, the adenylate cyclase inhibitor of the present invention can be SQ22536. In the present invention, a commercially available adenylate cyclase inhibitor can be obtained. Alternatively, an adenylate cyclase inhibitor can be produced by a method known to those skilled in the art. If the adenylate cyclase inhibitor of the present invention is a compound, the adenylate cyclase inhibitor of the present invention includes a pharmaceutically acceptable salt of such compound (preferably, for example, a sodium or calcium salt).

When a protein kinase A (PKA) inhibitor or an adenylate cyclase inhibitor is used as the preventive and/or therapeutic drug for cartilaginous hyperplasia of the present invention, it can be prepared in accordance with common practice. Examples of the dosage form of a composition for oral administration include solid or liquid dosage forms, specific examples of which include tablets (such as sugar-coated tablets and film-coated tablets), pills, granules, powders, capsules (such as soft capsules), syrups, emulsions, and suspensions. Meanwhile, examples of the dosage form of a composition for parenteral administration that can be used include injections and suppositories. Injections may be in the dosage form of intravenous injection, subcutaneous injection, intradermal injection, intramuscular injection, drip injection, or the like. Injections for intra-articular administration are more preferable. These formulations are prepared by a known method using additives, examples of which include excipients (e.g., organic excipients (including sugar derivatives such as lactose, sucrose, glucose, mannitol, and sorbitol; starch derivatives such as corn starch, potato starch, α-starch, and dextrin; cellulose derivatives such as crystalline cellulose; gum arabic; dextran; and pullulan) and inorganic excipients (including silicate derivatives such as light anhydrous silicic acid, synthetic aluminum silicate, calcium silicate, and magnesium aluminometasilicate; phosphates such as calcium hydrogen phosphate; carbonates such as calcium carbonate; and sulfates such as calcium sulfate)), lubricants (e.g., stearic acid and metal stearates such as calcium stearate and magnesium stearate; talc; colloidal silica; waxes such as beeswax and spermaceti; boric acid; adipic acid; sulfates such as sodium sulfate; glycol; fumaric acid; sodium benzoate; DL leucine; lauryl sulfates such as sodium lauryl sulfate and magnesium lauryl sulfate; silicic acids such as silicic acid anhydride and silicic acid hydrate; and the above starch derivatives), binders (e.g., hydroxypropyl cellulose, hydroxypropyl methylcellulose, polyvinylpyrrolidone, macrogol, and compounds listed above as excipients), disintegrants (e.g., cellulose derivatives such as low-substituted hydroxypropyl cellulose, carboxymethylcellulose, calcium carboxymethylcellulose and internally cross-linked sodium carboxymethylcellulose; and chemically modified starch/cellulose such as carboxymethyl starch, sodium carboxymethyl starch and cross-linked polyvinylpyrrolidone), emulsifiers (e.g., colloidal clay such as bentonite or VEEGUM; metal hydroxides such as magnesium hydroxide and aluminum hydroxide; anionic surfactants such as sodium lauryl sulfate and calcium stearate; cationic surfactants such as benzalkonium chloride; and nonionic surfactants such as polyoxyethylene alkyl ether, polyoxyethylene sorbitan fatty acid ester, and sucrose fatty acid ester), stabilizers (parahydroxybenzoate such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid), corrigents (e.g., sweeteners, acidulants and flavourings generally used), and diluents.

The dose of a drug administered to a patient according to the present invention varies depending on type of pathological condition to be treated, severity of symptoms and disease, patient's age, gender, and body weight, route of administration, and the like. Therefore, it cannot be unequivocally determined; however, a physician can determine an appropriate dose based on his/her decision in consideration of the above conditions.

<Method of Screening for a Therapeutic and/or Preventive Drug for Cartilaginous Hyperplasia>

According to the present invention, a method of screening for a test substance of a therapeutic and/or preventive drug for cartilaginous hyperplasia using indexes, which comprises bringing chondroprogenitor cells into contact with the test substance, is provided. Specifically, the present invention encompasses a method of screening for a therapeutic and/or preventive drug for cartilaginous hyperplasia, comprising the following steps of: (a) culturing chondroprogenitor cells under conditions in which the cells are brought into contact with a test substance and conditions in which the cells are not brought into contact with the test substance; (b) determining the index value for cells obtained in step (a); and (c) if the index value is lower under conditions in which the cells are brought into contact with a test substance than under conditions in which the cells are not brought into contact with the test substance, selecting the test substance as a therapeutic drug or preventive drug for cartilaginous hyperplasia.

The index used for screening in the present invention is at least one selected from the group consisting of SOX9 promoter activity, cAMP level, CREB phosphorylation, extracellular matrix volume, and volume of tissue containing chondrocytes.

Although a method for detecting SOX9 promoter activity in the present invention is not particularly limited, if chondroprogenitor cells have a reporter gene which is expressed under the regulation of an SOX9 promoter, the expression of the reporter gene is detected. In another embodiment, SOX9 promoter activity can be detected by detecting the expression of endogenous SOX9. Examples of reporter genes include genes encoding fluorescent proteins such as green fluorescent protein (GFP), yellow fluorescent protein (YFP), and blue fluorescent protein (BFP), photoproteins such as aequorin, and enzymes such as luciferase, β-galactosidase, alkaline phosphatase, and horseradish peroxidase (HRP).

In order to detect SOX9 promoter activity, chondrocytes into which a construct having a nucleotide sequence obtained by binding an SOX9 promoter region and a reporter gene has been introduced can be used. Here, a DNA fragment including an SOX9 promoter region can be isolated from genomic DNA or a genomic library by a method known to those skilled in the art. A preferable promoter region in the present invention is a nucleotide sequence set forth in SEQ ID NO: 9. The construct is produced using a plasmid vector, a viral vector, or an artificial chromosome vector (Suzuki N et al., J Biol Chem. 281(36): 26615, 2006).

In another embodiment, if the chondroprogenitor cells are produced from pluripotent stem cells, they may be prepared from pluripotent stem cells obtained using a genetic technique for inserting a reporter gene that is regulated by an SOX9 promoter by substituting the SOX9 coding region with the reporter gene sequence via homologous recombination. Alternatively, they may be prepared from pluripotent stem cells obtained using a genetic technique for inserting a reporter gene sequence into the SOX9 locus to produce a fusion protein of a protein encoded by SOX9 or a portion thereof and a protein encoded by the reporter gene.

When expression of the reporter gene or endogenous SOX9 is detected, transcripts (e.g., hnRNA and mRNA) may be detected by PCR, LAMP, northern hybridization, or the like. Translation products (e.g., peptides such as modified peptides) may be detected by RIA, IRMA, EIA, ELISA, LPIA, CLIA, immunoblotting, or the like. It is desirable to quantitatively detect transcripts and translation products.

In the present invention, when the cAMP level is used as an index, an arbitrary method known in the art can be used. For example, detection can be performed by RIA, IRMA, EIA, ELISA, LPIA, or CLIA.

In the present invention, when CREB phosphorylation is used as an index, an arbitrary method known in the art can be used. For example, detection can be performed by western blotting using an antibody capable of specifically recognizing phosphorylated CREB.

An extracellular matrix component used as an index in the present invention is not particularly limited as long as it is an extracellular matrix of cartilage tissue. Examples thereof include type II collagen, proteoglycan (aggrecan), hyaluronic acid, and glycosaminoglycan. An extracellular matrix component used as a particularly preferable index is glycosaminoglycan. When an extracellular matrix component is used as an index, an arbitrary method known in the art can be used. For example, when glycosaminoglycan is used as an index, Blyscan Glycosaminoglycan Assay (Biocolor) can be used, but a method used herein is not limited thereto.

In the present invention, when the volume of tissue containing chondrocytes is used as an index, an arbitrary method known in the art can be used. For example, it is possible to determine the volume based on an image stained with Alcian blue. Determination is possible via visual observation. Alternatively, mechanical detection with the use of an IN Cell Analyzer or the like is also possible.

Chondroprogenitor cells having an NLRP3 mutation can be used for detection of further remarkable differences in an index in order to screen for a test substance of the therapeutic and/or preventive drug for cartilaginous hyperplasia of the present invention. Chondroprogenitor cells having an NLRP3 mutation can be directly collected from an individual having such mutation. Alternatively, chondroprogenitor cells can be induced from pluripotent stem cells having an NLRP3 mutation. Examples of an NLRP3 mutation include, but are not limited to, mutations associated with chronic infantile neurological cutaneous and articular syndrome, such as, Tyr570Cys and Gly307Ser.

In the present invention, pluripotent stem cells having an NLRP3 mutation can be obtained by inserting the mutation into pluripotent stem cells via homologous recombination. When iPS cells are used as pluripotent stem cells, iPS cells may be produced from somatic cells having such mutation.

In order to screen for a test substance of the therapeutic and/or preventive drug for cartilaginous hyperplasia of the present invention, a culture method that comprises inducing chondroprogenitor cells to differentiate into chondrocytes during culture under conditions in which the chondroprogenitor cells are brought into contact with a test substance may be used for detecting further remarkable differences in an index.

An arbitrary test substance can be used in the screening method of the present invention, and it may be any conventional or novel compound. Examples thereof include a cell extract, a cell culture supernatant, a microbial fermentation product, a marine-derived extract, a plant extract, a purified or crude protein, a peptide, a non-peptide compound, a synthetic low-molecular-weight compound, and a naturally occurring compound. In the present invention, a test substance can also be obtained by any of a variety of combinatorial library approaches known in the art, which include the following: (1) a biological library method, (2) a synthetic library method using deconvolution; (3) a "one-bead one-compound" library method; and (4) a synthetic library method using affinity chromatography selection. Although application of a biological library method using affinity chromatography selection is limited to a peptide library, the other approaches can be applied to a peptide library, a non-peptide oligomer library, and a compound library such as a low-molecular-weight compound library (Lam (1997) Anticancer Drug Des. 12: 145-67). Examples of a molecular library synthesis method can be found in the art (see DeWitt et al. (1993) Proc. Natl. Acad. Sci. USA 90: 6909-13; Erb et al. (1994) Proc. Natl. Acad. Sci. USA 91: 11422-6; Zuckermann et al. (1994) J. Med. Chem. 37: 2678-85; Cho et al. (1993) Science 261: 1303-5; Carell et al. (1994) Angew. Chem. Int. Ed. Engl. 33: 2059; Carell et al. (1994) Angew. Chem. Int. Ed. Engl. 33: 2061; Gallop et al. (1994) J. Med. Chem. 37: 1233-51). A compound library can be produced as a library containing the following: solutions (Houghten (1992) Bio/Techniques 13: 412-21) or beads (Lam (1991) Nature 354: 82-4); chips (Fodor (1993) Nature 364: 555-6); bacteria (U.S. Pat. No. 5,223,409); spores (U.S. Pat. Nos. 5,571,698, 5,403,484, and 5,223,409); and plasmids (Cull et al. (1992) Proc. Natl. Acad. Sci. USA 89: 1865-9) or phages (Scott and Smith (1990) Science 249: 386-90; Devlin (1990) Science 249: 404-6; Cwirla et al. (1990) Proc. Natl. Acad. Sci. USA 87: 6378-82; Felici (1991) J. Mol. Biol. 222: 301-10; US Patent Application No. 2002103360).

Preferable examples of target diseases for the screening method of the present invention include chronic infantile neurological cutaneous and articular syndrome.

Chondroprogenitor cells used for screening of the present invention may be produced from pluripotent stem cells via differentiation induction. As a differentiation induction method, an arbitrary method used in the art can be employed. Not only methods known to those skilled in the art at the time of filing of the present application but also differentiation induction methods that have been developed after the filing of the present application can be employed. Examples of a method for differentiation induction of chondrocytes include, but are not limited to, methods disclosed in the following: Koyama, N. et al. Stem Cells and Development 22, 102-113 (2013); Hwang, N. S., et al. PLoS ONE 3, e2498 (2008); Oldershaw, R. A. et al. Nat. Biotechnol. 28, 1187-1194 (2010); Bai, H. Y., et al. Journal of Biomedical Materials Research. Part A 94, 539-546 (2010); Umeda, K. et al. Scientific Reports 2 (2012); and Yamashita, A. et al. Scientific Reports 3 (2013).

In the present invention, the term "chondroprogenitor cells" refers to progenitor cells that grow in a specific manner into "chondrocytes" that produce an extracellular matrix including collagen, glycosaminoglycan (GAG), or the like to form cartilage or cartilage tissue. Chondroprogenitor cells are cells in which chondrocyte-specific genes are expressed to a weaker extent than in chondrocytes.

In the present invention, examples of chondrocyte-specific genes include type II collagen (COL2A1), SOX9, cartilage oligomeric matrix protein (COMP), and AGGRECAN (ACAN). In the present invention, examples of COL2A1 include a gene having a nucleotide sequence with NCBI Accession No. NM_001844 or NM_033150 for humans or NCBI Accession No. NM_001113515 or NM_031163 for mice, a protein encoded by the gene, and a naturally occurring mutant having functions of such gene or protein. In the present invention, examples of SOX9 include a gene having a nucleotide sequence with NCBI Accession No. NM_000346 for humans or NCBI Accession No. NM_011448 for mice, a protein encoded by the gene, and a naturally occurring mutant having functions of such gene or protein. In the present invention, examples of COMP include a gene having a nucleotide sequence with NCBI Accession No. NM_000095 for humans or NCBI Accession No. NM_016685 for mice, a protein encoded by the gene, and a naturally occurring mutant having functions of such gene or protein. In the present invention, examples of ACAN include a gene having a nucleotide sequence with NCBI Accession No. NM_001135 or NM_013227 for humans or NCBI Accession No. NM_007424 for mice, a protein encoded by the gene, and a naturally occurring mutant having functions of such gene or protein.

Chondroprogenitor cells used in the present invention are cells in which, among chondrocyte-specific genes, SOX9 and COL2A1 are expressed while COMP and ACAN are weakly expressed, not expressed, or unable to be confirmed as being expressed. In the present invention, when COMP and ACAN are weakly expressed, it means that the expression levels of the chondrocyte-specific genes are lower than those in chondrocytes.

Chondroprogenitor cells used in the present invention may form a population consisting of chondroprogenitor cells or they may be in the form of a culture (pellet) (of cartilage tissue) comprising chondroprogenitor cells and an extracellular matrix produced by the cells.

Differentiation induction into chondroprogenitor cells is carried out induced in accordance with, for example, the protocol described below (a modified version of Umeda, K. et al. Scientific Reports 2 (2012)). In this case, arbitrary differentiation-inducing factors are used. Examples of differentiation-inducing factors used in the present invention include, but are not limited to, Noggin, Bio, PDGF (preferably PDGF-BB), TGF-β, and BMP4. These factors can be added in any combination at any stage in a culture step for differentiation into chondroprogenitor cells. A preferable example of a method for differentiation induction includes the following steps: step (i) of inducing iPS cells to differentiate into mesodermal cells and step (ii) of inducing the cells obtained in step (i) to differentiate into chondrocytes; or step (i) of inducing iPS cells to differentiate into neural crest cells and step (ii) of inducing the cells obtained in step (i) to differentiate into chondroprogenitor cells. In the present invention, in order to mature chondroprogenitor cells, two-dimensional (2D) micromass culture or three-dimensional (3D) pellet culture may be further employed. Chondroprogenitor cells used in the present invention also include cells at the stage of preparing chondrocytes via two-dimensional (2D) micromass culture or three-dimensional (3D) pellet culture.

When chondroprogenitor cells used in the present invention are produced from pluripotent stem cells, the cells may be produced by a step of inducing mesodermal cells or neural crest cells from pluripotent stem cells.

In the present invention, the term "mesodermal cells" refers to cells that develop between the endoderm and ectoderm in the gastrulation phase of the animal embryonic development stage. Examples thereof include BRACHYURY-, KDR-, FOXF1-, FLK1-, and BMP4-positive cells. These marker genes may be expressed separately or in combination in mesodermal cells in the present invention. Preferably, mesodermal cells are cells in which KDR is expressed.

In the present invention, the term "neural crest cells" refers to cells equivalent to cells having the capacity to migrate to various intraembryonic sites that have delaminated from neural crests. Specifically, neural crest cells in the present invention include undifferentiated neural-crest-derived cells in neural-crest-derived tissues (e.g., bone marrow, dorsal root ganglion, heart, cornea, iris, pulp, and olfactory mucosa tissues). Preferably, neural crest cells are positive for at least one of TFAP2A-, SOX10-, PAX3-, or p75 (NGFR). In the present invention, TFAP2A includes a gene having a nucleotide sequence with NCBI Accession No. NM_001032280, NM_001042425, or NM_003220 for humans or NCBI Accession No. NM_001122948 or NM_011547 for mice, a protein encoded by the gene, and a naturally occurring mutant having functions of such gene or protein. In the present invention, SOX10 includes a gene having a nucleotide sequence with NCBI Accession No. NM_006941 for humans or NCBI Accession No. NM_011437 for mice, a protein encoded by the gene, and a naturally occurring mutant having functions of such gene or protein. In the present invention, PAX3 includes a gene having a nucleotide sequence with NCBI Accession No. NM_000438, NM_001127366, NM_013942, NM_181457, NM_181458, NM_181459, NM_181460, or NM_181461 for humans or NCBI Accession No. NM_001159520 or NM_008781 for mice, a protein encoded by the gene, and a naturally occurring mutant having functions of such gene or protein. In the present invention, p75 (NGFR) includes a gene having a nucleotide sequence with NCBI Accession No. NM_002507 for humans or NCBI Accession No. NM_033217 for mice, a protein encoded by the gene, and a naturally occurring mutant having functions of such gene or protein.

<Step of Inducing Pluripotent Stem Cells to Differentiate into Mesodermal Cells>

In the present invention, a method of inducing mesodermal cells from pluripotent stem cells is not particularly limited. For example, a method comprising performing culture in a culture solution containing a BMP inhibitor and a GSK-3β inhibitor is illustrated.

In step (1) of inducing mesodermal cells from pluripotent stem cells, preferably, iPS cells obtained as described below can be separated by an arbitrary method so as to be cultured via suspension culture. Here, a method for separating cells involves, for example, mechanical separation or separation using separation solutions having protease activity and collagenase activity (e.g., Accutase™ and Accumax™) or a separation solution having collagenase activity alone. Preferably, pluripotent stem cells used herein are in the form of colonies of cells which have been cultured to become 80% confluent in a dish used for culture.

Suspension culture of the present invention means culturing cells in a culture dish in a non-adherent manner. Examples of a culture dish that can be used include, but are not limited to, a culture dish prepared without artificial treatment (e.g., coating treatment with the use of extracellular matrix or the like) for improving adhesion to cells and a culture dish prepared with artificial treatment for preventing adhesion (e.g., coating treatment with the use of poly (hydroxyethyl methacrylate) (poly-HEMA)).

A culture solution used for the induction of mesodermal cells from pluripotent stem cells can be prepared by adding a BMP inhibitor, a GSK-3β inhibitor, and a TGFβ family inhibitor to a basal medium used for animal cell culture. Examples of a basal medium include IMDM medium, Medium 199 medium, EMEM (Eagle's Minimum Essential Medium) medium, αMEM medium, DMEM (Dulbecco's Modified Eagle's Medium) medium, Ham's F12 medium, RPMI 1640 medium, Fischer's medium, and a medium mixture comprising any combination thereof. The medium may contain serum (e.g., FBS) or it may be serum-free medium. If necessary, the medium may contain at least one serum replacement such as albumin, transferrin, KnockOut Serum Replacement (KSR) (serum replacement for FBS in ES cell culture) (Invitrogen), N2 supplement (Invitrogen), B27 supplement (Invitrogen), fatty acid, insulin, sodium selenite, a collagen precursor, a trace element, 2-mercaptoethanol, or 3'-thioglycerol. In addition, it may contain at least one substance such as lipid, an amino acid, L-glutamine, GlutaMAX (Invitrogen), a non-essential amino acid (NEAA), a vitamin, a growth factor, a low-molecular-weight compound, an antibiotic, an antioxidant, pyruvic acid, a buffering agent, or an inorganic salt. In one embodiment, the basal medium used for induction of mesodermal cells from pluripotent stem cells is a medium mixture containing IMDM medium and Ham's F12 medium at 1:1.

In the present invention, any BMP inhibitor can be used as long as it is a substance involved in the inhibition of BMP signal transduction (BMP signaling) via binding between BMP (bone morphogenetic protein) and a BMP receptor (type I or II). Examples thereof include, but are not limited to, Dorsomorphin (i.e., 6-[4-(2-piperidin-1-yl-ethoxy)phenyl]-3-pyridin-4-yl-pyrazolo[1,5-a]pyrimidine) and a derivative thereof (P. B. Yu et al. (2007), Circulation, 116: II_60; P. B. Yu et al. (2008), Nat. Chem. Biol., 4:33-41; J. Hao et al. (2008), PLoS ONE (www.plozone.org), 3(8): e2904), Noggin, chordin, and follistatin. These inhibitors are available from, for example, R&D systems, or they may be self-prepared. A preferable BMP inhibitor used in the present invention is Noggin. Noggin includes Noggin from humans or non-human animals and a functional variant thereof. For example, a commercially available Noggin provided by R&D systems or the like can be used. The concentration of a BMP inhibitor used in the present invention can be appropriately determined by those skilled in the art depending on a BMP inhibitor to be used. For example, when Noggin is used as a BMP inhibitor, the concentration is 1 ng/ml to 500 ng/ml and preferably 10 ng/ml to 200 ng/ml, e.g., 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 120 ng/ml, 140 ng/ml, 160 ng/ml, 180 ng/ml, or 200 ng/ml, but it is not limited thereto. Further preferably, it is 100 ng/ml.

In the present invention, a GSK-3β inhibitor is not particularly limited as long as it can directly or indirectly inhibit a function of GSK-3β such as kinase activity. Examples thereof include, but are not limited to, Wnt3a, BIO (also known as a GSK-3β inhibitor IX; 6-bromoindirubin-3'-oxime), which is an indirubin derivative, SB216763 (3-(2, 4-dichlorophenyl)-4-(1-methyl-1H-indole-3-yl)-1H-pyrrole-2,5-dione), which is a maleimide derivative, a GSK-3β inhibitor VII (4-dibromoacetophenone), which is a phenyl-α-bromomethyl ketone compound, L803-mts (also known as a GSK-3β peptide inhibitor; Myr-N-GKEAPPAPPQSpP-NH$_2$), which is a cell transmembrane phosphorylated peptide, and CHIR99021 (Nature (2008) 453: 519-523) having high selectivity. These compounds are available from, for example, Stemgent, Calbiochem, and Biomol, or they may be self-prepared. A preferable GSK-3β inhibitor used in the present invention is BIO. BIO includes a functional variant thereof. An example of such functional variant is Acetoxime-BIO (AceBIO). Although the concentration of a GSK-3β inhibitor used in the present invention can be appropriately determined by those skilled in the art depending on a GSK-3β inhibitor to be used, for example, when Bio is used as a GSK-3β inhibitor, the concentration is 0.1 μM to 100 μM and preferably 0.5 μM to 20 μM such as 0.5 μM, 1 μM, 1.5 μM, 2 μM, 3 μM, 4 μM, 5 μM, 6 μM, 7 μM, 8 μM, 9 μM, 10 μM, 15 μM, or 20 μM, but it is not limited thereto. Further preferably, it is 2 μM to 5 μM. The concentration of a GSK-3β inhibitor used in the present invention can be changed during a step. For example, when Bio is used as a GSK-3β inhibitor, it is possible to set the concentration to 3 μM from day 0 to day 3 and 5 μM from day 4 to day 8.

In the present invention, a TGFβ family inhibitor is not particularly limited as long as it is a low-molecular-weight inhibitor that interferes TGFβ family signal transduction. Examples thereof include SB431542, SB202190 (R. K. Lindemann et al., Mol. Cancer 2:20 (2003)), SB505124 (Glaxo SmithKline), NPC30345, SD093, SD908, SD208 (Scios), LY2109761, LY364947, LY580276 (Lilly Research Laboratories), and A-83-01 (WO 2009/146408). A preferable GSK-3β inhibitor used in the present invention is SB431542. The concentration of a TGFβ family inhibitor used in the present invention can be appropriately determined by those skilled in the art depending on a TGFβ family inhibitor to be used. For example, when SB431542 is used as a TGFβ family inhibitor, the concentration is 0.1 μM to 100 μM and preferably 0.5 μM to 20 μM such as 0.5 μM, 1 μM, 1.5 μM, 2 μM, 3 μM, 4 μM, 5 μM, 6 μM, 7 μM, 8 μM, 9 μM, 10 μM, 15 μM, or 20 μM, but it is not limited thereto. Further preferably, it is 2 μM to 5 μM. The concentration of a GSK-3β inhibitor used in the present invention can be changed during a step. For example, when Bio is used as a GSK-3β inhibitor, it is possible to set the concentration to 3 μM from day 0 to day 3 and 5 μM from day 4 to day 8.

In step (i) used for induction of mesodermal cells from pluripotent stem cells, although the culture temperature is not particularly limited, it is approximately 30° C. to 40° C. and preferably approximately 37° C. Culture is performed in an atmosphere of air containing $CO_2$. The $CO_2$ concentration is approximately 2% to 5% and preferably approximately 5%. The culture period in this step is, for example, 15 days or less, preferably 9 days or less, and more preferably 5 days or less.

The term "pluripotent stem cells" used in the present invention refers to stem cells having pluripotent capacity to differentiate into all types of cells present in vivo and proliferative capacity. Examples of pluripotent stem cells include, but are not particularly limited to, embryonic stem (ES) cells (J. A. Thomson et al. (1998), Science 282: 1145-1147; J. A. Thomson et al. (1995), Proc. Natl. Acad. Sci. USA, 92: 7844-7848; J. A. Thomson et al. (1996), Biol. Reprod., 55: 254-259; J. A. Thomson and V. S. Marshall (1998), Curr. Top. Dev. Biol., 38: 133-165), nuclear transfer embryonic stem (ntES) cells from a cloned embryo (T. Wakayama et al. (2001), Science, 292: 740-743; S. Wakayama et al. (2005), Biol. Reprod., 72: 932-936; J. Byrne et al. (2007), Nature, 450:497-502), germline stem cells ("GS cells") (M. Kanatsu-Shinohara et al. (2003) Biol. Reprod., 69:612-616; K. Shinohara et al. (2004), Cell, 119:1001-1012), embryonic germ cells ("EG cells") (Y. Matsui et al. (1992), Cell, 70: 841-847; J. L. Resnick et al. (1992), Nature, 359: 550-551), induced pluripotent stem (iPS) cells (K. Takahashi and S. Yamanaka (2006) Cell, 126: 663-676; K. Takahashi et al. (2007), Cell, 131: 861-872; J. Yu et al. (2007), Science, 318: 1917-1920; Nakagawa, M. et al., Nat. Biotechnol. 26: 101-106 (2008); WO 2007/069666), and culture-fibroblast- or bone-marrow-stem-cell-derived pluripotent cells (Muse cells) (WO2011/007900). Further preferably, pluripotent stem cells are human pluripotent stem cells.

Pluripotent stem cells used in the present invention are desirably pluripotent stem cells having an NLRP3 mutation, and thus, they are preferably iPS cells produced from somatic cells from cartilaginous hyperplasia patients.

In order to detect further remarkable differences in an index for screening for a test substance of the therapeutic and/or preventive drug for cartilaginous hyperplasia of the present invention, a culture method comprising inducing chondroprogenitor cells to differentiate into chondrocytes may be used for culture under conditions in which the chondroprogenitor cells are brought into contact with a test substance.

<(i) Step of Inducing Pluripotent Stem Cells to Differentiate into Neural Crest Cells>

In the present invention, although a method for inducing neural crest cells from pluripotent stem cells is not particularly limited, an example thereof is a method comprising performing culture in a culture solution containing a TGFβ family inhibitor.

In step (i) of inducing neural crest cells from pluripotent stem cells, it is possible to induce pluripotent stem cells obtained in the above manner by, preferably, culturing the pluripotent stem cells via adhesion culture and then replacing the culture solution.

In the present invention, in order to improve capacity of pluripotent stem cells to adhere to a culture container, a culture container subjected to coating can be used for adhesion culture. Examples of a coating agent include Matrigel (BD Biosciences), Synthemax (Corning), collagen, gelatin, laminin, heparan sulfate proteoglycan, entactin, fibronectin, and fractions and combinations thereof. Preferably, a coating agent is Matrigel.

A culture solution used for the induction of neural crest cells from pluripotent stem cells can be prepared by adding a TGFβ family inhibitor to a basal medium used for animal cell culture. Examples of a basal medium include IMDM medium, Medium 199 medium, EMEM (Eagle's Minimum Essential Medium) medium, αMEM medium, DMEM (Dulbecco's Modified Eagle's Medium) medium, Ham's F12 medium, RPMI 1640 medium, Fischer's medium, and a medium mixture comprising any combination thereof. The medium may contain serum (e.g., FBS) or it may be serum-free medium. If necessary, the medium may contain at least one serum replacement such as albumin, transferrin, Knock-Out Serum Replacement (KSR) (a serum replacement for ES cells culture) (Invitrogen), N2 supplement (Invitrogen), B27 supplement (Invitrogen), fatty acid, insulin, sodium selenite, a collagen precursor, a trace element, 2-mercaptoethanol, or 3'-thioglycerol. It also may contain at least one substance such as lipid, an amino acid, L-glutamine, GlutaMAX (Invitrogen), a non-essential amino acid (NEAA), a vitamin, a growth factor, a low-molecular-weight compound, an antibiotic, an antioxidant, pyruvic acid, a buffering agent, or an inorganic salt. In one embodiment of the use of a basal medium for the induction of neural crest cells from pluripotent stem cells, a preferable basal medium is a medium mixture comprising IMDM medium and Ham's F12 medium at 1:1, which is supplemented with serum, GlutaMAX, insulin, transferrin, vitamins, and 3'-thioglycerol.

A TGFβ family inhibitor used for the induction of neural crest cells from pluripotent stem cells can be used under the conditions that apply to the aforementioned TGFβ family inhibitor.

In step (i) used for the induction of neural crest cells from pluripotent stem cells, the culture temperature is not particularly limited, however, it is approximately 30° C. to 40° C. and preferably approximately 37° C., and culture is performed in an atmosphere of air containing $CO_2$. The $CO_2$ concentration is approximately 2% to 5% and preferably approximately 5%. The culture period in this step is, for example, 15 days or less and preferably 8 days for culture.

<(ii) Step of Inducing Mesodermal Cells or Neural Crest Cells to Differentiate into Chondrocytes>

In order to induce mesodermal cells or neural crest cells obtained in step (i) above to differentiate into chondrocytes, the cells are separated by an arbitrary method in step (ii). Step (ii) further includes step (ii-1) of inducing chondroprogenitor cells via adhesion culture; and step (ii-2) of inducing chondrocytes by a two-dimensional (2D) micromass culture method or step (ii-2') of inducing chondrocytes by a three-dimensional (3D) pellet culture method. Here, a mechanical method or an enzymatic method can be used as a method for separating mesodermal cells or neural crest cells. Preferably, the cells can be separated using TrypLE Select. In addition, after separating cells obtained in step (i) above, it is possible to concentrate mesodermal cells or neural crest cells using flow cytometry (FACS) so as to use them as starting cells in this step.

<(ii-1) Step for Inducing Chondroprogenitor Cells Via Adhesion Culture>

In the present invention, an example of a method for adhesion culture of mesodermal cells or neural crest cells is a method for culture using a culture container coated with an extracellular matrix. Coating can be carried out by introducing a solution containing an extracellular matrix into a culture container and removing the solution in an appropriate manner.

In the present invention, an extracellular matrix has an extracellular supramolecular architecture, and it may comprise a naturally-derived or artificial material (recombinant). Examples of components thereof include substances such as collagen, proteoglycan, fibronectin, hyaluronic acid, tenascin, entactin, elastin, fibrillin, and laminin, and fragments thereof. These extracellular matrix components may be used in combination. For example, a preparation obtained from cells (e.g., BD Matrigel™) may be used. An example of an artificial material is a laminin fragment. In the present invention, laminin is a protein having a heterotrimeric structure comprising an α chain, a β chain, and a γ chain. In one example of laminin, the α chain is α1, α2, α3, α4, or α5, the β chain is β1, β2, or β3, and the γ chain is γ1, γ2, or γ3, but they are not limited thereto. In the present invention, although a laminin fragment is not particularly limited as long as it is a laminin fragment having integrin binding activity, an example thereof is an E8 fragment obtained via elastase digestion. For adhesion culture for the induction of chondroprogenitor cells in the present invention, it is preferable that the culture container be coated with fibronectin.

A culture solution used in step (ii-1) of inducing chondroprogenitor cells from mesodermal cells or neural crest cells via adhesion culture in the present invention can be prepared by adding bFGF and a TGFβ family inhibitor to a basal medium used for animal cell culture. Examples of the basal medium include IMDM medium, Medium 199 medium, EMEM (Eagle's Minimum Essential Medium) medium, αMEM medium, DMEM (Dulbecco's Modified Eagle's Medium) medium, Ham's F12 medium, RPMI 1640 medium, Fischer's medium, and a medium mixture comprising any combination thereof. The medium may contain serum (e.g., FBS) or it may be serum-free medium. If necessary, the medium may contain at least one serum replacement such as albumin, transferrin, KnockOut Serum Replacement (KSR) (a serum replacement for FBS in ES cells culture) (Invitrogen), N2 supplement (Invitrogen), B27 supplement (Invitrogen), fatty acid, insulin, sodium selenite, a collagen precursor, a trace element, 2-mercaptoethanol, or 3'-thioglycerol. It also may contain at least one substance such as lipid, an amino acid, L-glutamine, GlutaMAX (Invitrogen), a non-essential amino acid (NEAA), a vitamin, a growth factor, a low-molecular-weight compound, an antibiotic, an antioxidant, pyruvic acid, a buffering agent, or an inorganic salt. In one embodiment of the use of a basal medium for the induction of neural crest cells from pluripotent stem cells, a preferable basal medium is a medium mixture comprising IMDM medium and Ham's F12 medium at 1:1, which is supplemented with serum, GlutaMAX, insulin, transferrin, vitamins, and 3'-thioglycerol.

A TGFβ family inhibitor used in step (ii-1) of inducing chondroprogenitor cells from mesodermal cells or neural crest cells via adhesion culture in the present invention can be used under the conditions that apply to the aforementioned TGFβ family inhibitor.

Commercially available bFGF provided by WAKO or the like can be used as bFGF used in step (ii-1) of inducing chondroprogenitor cells from mesodermal cells or neural crest cells via adhesion culture in the present invention. The concentration of bFGF is, for example, 0.1-100 ng/ml and preferably 1-50 ng/ml such as 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 30 ng/ml, 40 ng/ml, or 50 ng/ml, but it is not limited thereto. Further preferably, it is 5 ng/ml.

In step (ii-1) of inducing chondroprogenitor cells from mesodermal cells or neural crest cells via adhesion culture in the present invention, although the culture temperature is not particularly limited, it is approximately 30° C. to 40° C. and preferably approximately 37° C. Culture is performed in an atmosphere of air containing $CO_2$. The $CO_2$ concentration is approximately 2% to 5% and preferably approximately 5%. The culture period in this step is, for example, 15 days or less and preferably 9 days for culture.

<(ii-2) Two-Dimensional (2D) Micromass Culture Method>

In the present invention, a two-dimensional (2D) micromass culture method can be carried out by performing culture using a culture container coated with an extracellular matrix. Coating can be carried out by introducing a solution containing an extracellular matrix into a culture container and removing the solution in an appropriate manner.

In the present invention, micromass culture is a culture method comprising seeding a small amount of a culture solution (e.g., 1 μl to 50 μl and preferably 1 μl to 10 μl) with cells at a high density (e.g., 10000 cells to 1000000 cells, and preferably 10000 cells to 500000 cells) for culture.

In the present invention, an extracellular matrix is an extracellular supramolecular architecture, and it may comprise a naturally-derived or artificial material (recombinant). Examples of components thereof include substances such as collagen, proteoglycan, fibronectin, hyaluronic acid, tenascin, entactin, elastin, fibrillin, and laminin, and fragments thereof. These extracellular matrix components may be used in combination. For example, an extracellular matrix may be a preparation from cells, such as, BD Matrigel™. An example of artificial material is a laminin fragment. In the present invention, laminin is a protein having a heterotrimeric structure having an α chain, a β chain, and a γ chain. In one example of laminin, the α chain is α1, α2, α3, α4, or α5, the β chain is β1, β2, or β3, and the γ chain is γ1, γ2, or γ3, but they are not limited thereto. In the present invention, although a laminin fragment is not particularly limited as long as it is a laminin fragment having integrin binding activity, an example thereof is an E8 fragment which is a fragment obtained via elastase digestion. For adhesion culture for the induction of chondroprogenitor cells in the present invention, it is preferable for a culture container to be coated with fibronectin.

A culture solution used in step (ii-2) can be prepared by adding PDGF-BB, TGFβ3, and BMP4 or equivalents thereof to a basal medium used for animal cell culture. These factors to be added to a basal medium may be added simultaneously or separately at an arbitrary stage of the culture step.

Examples of a functional equivalent of PDGF-BB include, but are not limited to, PDGF-AA, PDGF-AB, PDGF-CC, and PDGF-DD. Examples of a functional equivalent of TGFβ3 include, but are not limited to, TGFβ1 and TGFβ2. Examples of a functional equivalent of BMP4 include, but are not limited to, BMP2, BMP6, and BMP7.

Examples of a basal medium include IMDM medium, Medium 199 medium, EMEM (Eagle's Minimum Essential Medium) medium, αMEM medium, DMEM (Dulbecco's Modified Eagle's Medium) medium, Ham's F12 medium, RPMI 1640 medium, Fischer's medium, and a medium mixture comprising any combination thereof. The medium may contain serum (e.g., FBS) or it may be serum-free medium. If necessary, the medium may contain at least one serum replacement such as albumin, transferrin, KnockOut Serum Replacement (KSR) (a serum replacement for FBS in ES cells culture) (Invitrogen), N2 supplement (Invitrogen), B27 supplement (Invitrogen), fatty acid, insulin, sodium selenite, a collagen precursor, a trace element, 2-mercaptoethanol, or 3'-thioglycerol. It also may contain at least one substance such as lipid, an amino acid, L-glutamine, GlutaMAX (Invitrogen), a non-essential amino acid (NEAA), a vitamin, a growth factor, a low-molecular-weight compound, an antibiotic, an antioxidant, pyruvic acid, a buffering agent, or an inorganic salt. In one embodiment of this step, a basal medium is a serum-free chondrogenesis medium obtained by mixing DMEM medium and Ham's F12 medium at 1:1.

The concentration of PDGF-BB in a basal medium is, for example, 1-100 ng/ml and preferably 20-60 ng/ml such as 1 ng/ml, 10 ng/ml, 20 ng/ml, 25 ng/ml, 30 ng/ml, 35 ng/ml, 40 ng/ml, 50 ng/ml, 60 ng/ml, 70 ng/ml, 80 ng/ml, 90 ng/ml, or 100 ng/ml, but it is not limited thereto. Further preferably, it is 40 ng/ml.

The concentration of TGFβ3 in a basal medium is, for example, 1-100 ng/ml and preferably 5-20 ng/ml such as 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 25 ng/ml, 50 ng/ml, 75 ng/ml, or 100 ng/ml, but it is not limited thereto. Further preferably, it is 10 ng/ml.

The concentration of BMP4 in a basal medium is, for example, 1-200 ng/ml and preferably 20-40 ng/ml such as 1 ng/ml, 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 120 ng/ml, 140 ng/ml, 160 ng/ml, 180 ng/ml, or 200 ng/ml, but it is not limited thereto. Further preferably, it is 50 ng/ml.

In step (ii-2), although the culture temperature is not particularly limited, it is approximately 30° C. to 40° C. and preferably approximately 37° C. Culture is performed in an atmosphere of air containing $CO_2$. The $CO_2$ concentration is approximately 2% to 5% and preferably approximately 5%. The culture period in this step is, for example, 20 days or less and preferably 14 days or less for culture.

PDGF-BB, TGFβ3, and BMP4 may be added to a basal medium simultaneously or separately at an arbitrary stage of the culture step. Preferably, they are added in any combination in an arbitrary order in accordance with the stage of the culture step. Further, when PDGF-BB, TGFβ3, and BMP4 are added to a basal medium, they can be added directly to a medium during culture or upon medium replacement.

In this step, the following combination of PDGF-BB, TGFβ3, and BMP4 can be added to a basal medium in the following order:
(1) PDGF-BB,
(2) PDGF-BB and TGFβ3, and
(3) BMP4.

The culture period in step (1) is, for example, 10 days or less and preferably 6 days for culture. The culture period in step (2) is, for example, 8 days or less and preferably 4 days for culture. The culture period in step (3) is, for example, 8 days or less and preferably 4 days for culture.

PDGF-BB, TGFβ3, and BMP4 may be added to a basal medium in combination with other differentiation-inducing factors. Examples of other differentiation-inducing factors include, but are not limited to, Wnt3A, Activin, FGF2, Follistatin, GDF5, and NT4.

<(ii-2') Three-Dimensional (3D) Pellet Culture Method>

The present invention may include a step of subculturing cells obtained in step (i) in a medium supplemented with FGF2 and TGFβ3 prior to 3D pellet culture. Although the subculture period is not particularly limited, it is 5 days or less and preferably 3 days. The concentration of FGF2 in a medium is, for example, 0.1-50 ng/ml and preferably 0.5-20 ng/ml such as 0.5 ng/ml, 0.6 ng/ml, 0.7 ng/ml, 0.8 ng/ml, 0.9 ng/ml, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 12 ng/ml, 14 ng/ml, 16 ng/ml, 18 ng/ml, or 20 ng/ml, but it is not limited thereto. Further preferably, it is 1 to 5 ng/ml. The concentration of TGFβ3 in a medium is, for example, 1-100 ng/ml and preferably 5-20 ng/ml such as 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 25 ng/ml, 50 ng/ml, 75 ng/ml, or 100 ng/ml, but it is not limited thereto. Further preferably, it is 10 ng/ml.

In the present invention, a step of centrifuging an aliquot of the cells subcultured above to form a pellet prior to 3D pellet culture may be further included. Although the number of cells to be centrifuged is not particularly limited, $2.5 \times 10^5$ cells can be centrifuged, for example.

A medium used in the 2D micromass culture method can be used for a culture solution used in step (ii-2').

In step (ii-2'), although the culture temperature is not particularly limited, it is approximately 30° C. to 40° C. and preferably approximately 37° C. Culture is performed in an atmosphere of air containing $CO_2$. The $CO_2$ concentration is approximately 2% to 5% and preferably approximately 5%. The culture period in this step is, for example, 40 days or less and preferably 28 days or less for culture.

Regarding the terms "cartilaginous pellet" and "cartilage tissue" used herein, the former refers to a population including chondrocytes induced via 3D pellet culture. Meanwhile, the term "cartilage tissue" refers to a population including chondrocytes induced using an arbitrary differentiation induction method as well as those induced via 3D pellet culture. The terms "cartilaginous pellet" and "cartilage tissue" used herein are interchangeable unless otherwise specified.

EXAMPLES

The present invention is described in more detail with reference to the following Examples. However, the scope of the present invention is not limited to the Examples.

Example 1

<Production of iPS Cells>

All of the experiments described below were conducted with the approval of the ethics committee of Kyoto University. In addition, sampling from patients was conducted with the preliminary acquisition of informed consent in accordance with the Declaration of Helsinki. iPS cells were produced from two NOMID patients having NLRP3 somatic mosaics (p.Tyr570Cys and p.Gly307Ser). At least three clones of wild-type NLRP3 iPS cells (hereinafter referred to as "wild-type iPS cells") and mutant-type NLRP3 iPS cells (hereinafter referred to as "mutant-type iPS cells") were established from each patient and used for the experiments. Every experiment described below was conducted by comparing wild-type cells and mutant-type cells having isogenic backgrounds.

iPS cells were produced by the following method. Specifically, each of the obtained human dermal fibroblasts (HDFs) was cultured in DMEM (Nacalai Tesque) medium supplemented with 10% FBS (Invitrogen), 0.5% penicillin, and streptomycin (Invitrogen). Next, OCT3/4, SOX2, KLF4, and c-MYC were introduced into fibroblasts capable of expressing the mouse Slc7a1 gene via ecotropic retroviral transduction (Tanaka, T., et al., Blood. 9; 120(6): 1299-308 (2012), and Takahashi, K., et al., Cell 131(5): 861-872 (2007)). Six days later, the cells were recovered and seeded on inactivated SNL feeder cells. On the following day, the medium was replaced with Primate ES cell medium (ReproCELL) supplemented with 4 ng/mL bFGF (Wako). Three weeks later, individual colonies were isolated and grown, and thereby iPS cells were obtained. Cell culture was performed at 37° C. in 5% $CO_2$ and 21% $O_2$.

Example 2

<Cartilage Induction>
1) Neural Crest Cell Induction (Days 0-8)

The iPS cells obtained in Example 1 were induced to differentiate into neural crest cells via feeder-free culture. First, the feeder cells were removed using CTK (0.25% Trypsin (Life Technologies), 0.1 mg/ml collagenase IV (Life Technologies), 1 mM CaCl, 20% (v/v) KSR), followed by washing with PBS. Then, the iPS cells were recovered using a scraper, suspended in mTeSR medium (mTeSR Basal Medium (400 ml), 5× Supplement (100 ml), Penicillin/Streptomycin (2.5 ml)) (STEMCELL Technology), and pipetted once. Subsequently, a Matrigel-coated dish (prepared by applying a Matrigel stock solution (×50) (BD Biosciences) diluted with DMEM/F12 medium (Life Technologies) to a dish was stored overnight at 4° C. Matrigel was removed 36 to 60 minutes before the use of the cells. The cells were dried and seeded ($5×10^4$/10-cm dish) on mTeSR medium (10 ml) and cultured at 37° C. in 5% $CO_2$. Two days later, the medium was replaced with neural crest induction medium (15 ml/10-cm dish). Specifically, the cells were cultured using a synthetic medium (CDM) supplemented with 10 uM SB431542 (Sigma-Aldrich) (medium containing: Iscove's modified Dulbecco's medium (Sigma-Aldrich) supplemented with 5 mg/ml fatty acid-free bovine serum albumin (Sigma-Aldrich), 2% (v/v) chemically defined Lipid concentrate (Life Technologies), 2 mM GlutaMax (Life Technologies), 100 µg/ml human holo-transferrin (Sigma-Aldrich), 20 µg/ml bovine insulin (Sigma-Aldrich), 0.45 mM MTG (monothioglycerol) (Sigma-Aldrich), and 0.17 mM AA2P (ascorbic acid-2-phosphate) (Sigma-Aldrich), and Ham's F12 (Life Technologies) at a mixing ratio of 1:1). The medium was replaced on day 5 of culture, and culture entered the chondroprogenitor cell induction stage on day 8 of culture.

2) Chondroprogenitor Cell Induction (Days 8-17)

The medium was removed. The cells were washed with PBS once, detached using Trypsin/EDTA (0.05%) (Life Technologies), and recovered using 10% FCS-containing CDM. The cells were separated using a 40-um Cell strainer (BD Biosciences) and then seeded on a fibronectin-coated dish (prepared by adding a fibronectin solution (Millipore) diluted 100-fold with PBS to a dish and allowing the dish to stand still at room temperature for 30 minutes to 60 minutes) ($2×10^6$/10-cm dish). Subculture was performed at a frequency of about once every three days using a neural crest induction medium supplemented with 5 ng/ml bFGF (WAKO), thereby allowing chondroprogenitor cells to grow.

3) Chondrocyte Induction (Starting from Day 17)
<Two-Dimensional (2D) Micromass Culture>

Chondroprogenitor cells ($1.5×10^5$ cells) obtained via the above method were suspended in a cartilage induction medium containing 40 ng/ml PDGF-BB and 1% FCS and the suspension was spotted in the form of 5-ml drops on a fibronectin-coated 24-well plate (BD), followed by culture. In this case, the medium was replaced every three days. Six days later, 10 ng/ml TGFβ3 was further added for culture. Ten days after the start of 2D micromass culture, PDGF-BB was substituted with 50 ng/ml BMP4 (WAKO). 2D micromass culture was performed at 37° C. in 5% $CO_2$ for 14 days.

<3D Pellet Culture>

Chondroprogenitor cells obtained by the above method were cultured in a cartilage induction medium containing 5 ng/mL FGF2 and 10 ng/ml TGFβ3 for 3 days. Then, $2.5×10^5$ cells were centrifuged to form a pellet, followed by culture in a cartilage induction medium containing 0.5 ml of 40 ng/ml PDGF-BB and 1% FCS, as in the case of 2D micromass culture. Six days later, 10 ng/ml TGFβ3 was further added for culture. Ten days later, PDGF-BB was substituted with 50 ng/ml BMP4 (WAKO). 3D pellet culture was mained at 37° C. in 5% $CO_2$ for 28 days.

The outline of the protocol for induction of chondrocytes from pluripotent stem cells described above is shown in FIG. 1A.

In order to examine the chondrocytes induced via 2D micromass culture and those induced via 3D pellet culture, the cells obtained by 2D micromass culture were fixed with 4% paraformaldehyde (PFA) for 1 hour and stained with 1% Alcian Blue (pH 1.0) (Sigma-Aldrich), and the cells obtained by 3D pellet culture were fixed with 4% paraformaldehyde (PFA) for 1 hour and stained with 0.1% Alcian Blue (pH 1.0) (Sigma-Aldrich). Further, immunostaining was carried out using an anti-COL2 antibody (Thermo Scientific). Alcian blue is a reagent for detecting an extracellular matrix secreted by chondrocytes, and COL2 is a gene that is expressed in a chondrocyte-specific manner.

As a result of staining, chondrocytes induced from either wild-type or mutant-type iPS cells were found to be Alcianblue-positive and COL2-positive (FIG. 1B). This indicates that the cells were successfully induced to differentiate into chondrocytes via 2D micromass culture and 3D pellet culture. In addition, when the sizes of chondrocyte cultures obtained through induction via 2D micromass culture and 3D pellet culture were measured, the size of mutant-type iPSC-derived chondrocytes was remarkably greater than that of wild-type iPSC-derived chondrocytes (FIG. 1C). Accordingly, cartilaginous hyperplasia, which is observed in NOMID patients, was successfully reproduced in vitro with the use of iPS cells from NOMID patients.

Example 3

<Analysis of the Expression of Chondrocyte-Specific Genes>

In order to further examine the details of the state of chondrocytes obtained through differentiation induction by the methods (2D micromass culture and 3D pellet culture) used in Example 2, chondroprogenitor cells before induction of chondrocytes and induced chondrocytes were examined to analyze the expression state of genes specifically expressed in chondrocytes (chondrocyte-specific genes). Gene expression analysis was conducted using the following method.

<Quantitative Determination of mRNA> mRNA was isolated from each cell using an RNeasy Mini Kit (Qiagen). cDNA was synthesized via reverse transcription using 1 µg of the obtained total RNA as a template and a Superscript III reverse transcriptase (Invitrogen). A standard curve for quantitative real-time PCR was created to conduct analysis. Real-time PCR analysis was conducted using a Power SYBR Green qPCR mastermix (Invitrogen) and a StepOne real-time PCR system (ABI) for quantitative determination. Table 1 lists the primer sequences and assay IDs.

TABLE 1

| Primer name | Sequence (5'→3') | Application |
|---|---|---|
| hSOX9 S1177 | GACTTCCGCGACGTGGAC (SEQ ID NO: 1) | SOX9 RT-qPCR |
| hSOX9 AS1275 | GTTGGGCGGCAGGTACTG (SEQ ID NO: 2) | |
| hCOL2 S4454 | GGCAATAGCAGGTTCACGTACA (SEQ ID NO: 3) | COL2A1 RT-qPCR |
| hCOL2 AS4532 | CGATAACAGTCTTGCCCCACTT (SEQ ID NO: 4) | |
| hCOMP-F | CAACTGTCCCCAGAAGAGCAA (SEQ ID NO: 5) | COMP RT-qPCR |
| hCOMP-R | TGGTAGCCAAAGATGAAGCCC (SEQ ID NO: 6) | |
| hACAN S790 | TCGAGGACAGCGAGGCC (SEQ ID NO: 7) | ACAN RT-qPCR |
| hACAN AS874 | TCGAGGGTGTAGCGTGTAGAGA (SEQ ID NO: 8) | |

Figure 2:
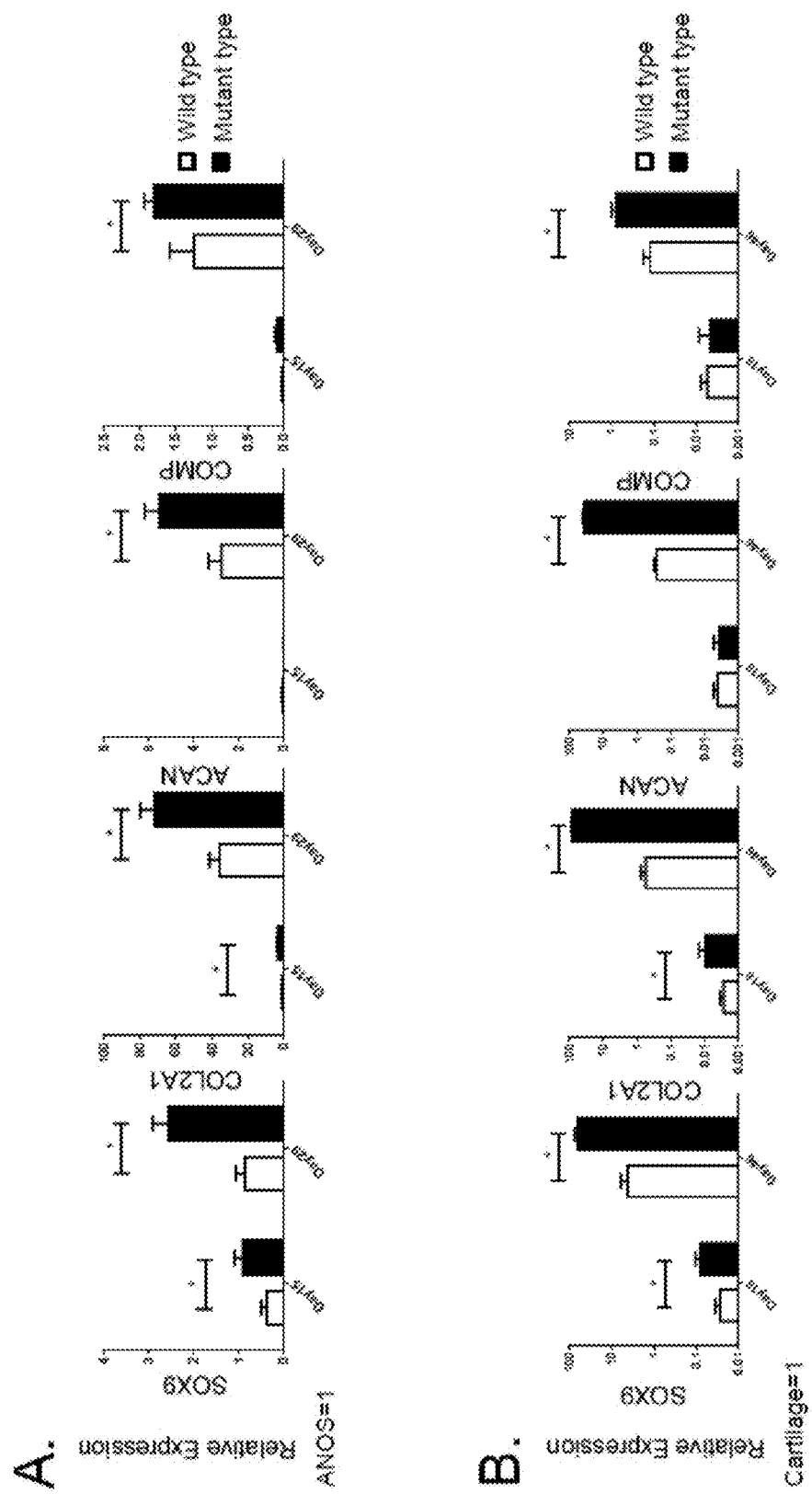
FIGS. 2A and 2B show results of the expression of chondrocyte-specific genes (SOX9, COL2A1, ACAN, and COMP) in wild-type iPSC- and mutant-type iPSC-derived chondroprogenitor cells (Day 15) and chondrocytes (Day 29).

As a result of quantitative PCR, the expression of chondrocyte-specific genes (namely, COL2A1, ACAN, COMP, and SOX9) was confirmed in chondrocytes induced from either wild-type or mutant-type iPS cells in both cases of 2D micromass culture and 3D pellet culture (FIG. 2). Further, in both cases of 2D micromass culture and 3D pellet culture, mutant-type iPSC-derived chondrocytes tended to have higher expression levels of the respective chondrocyte-specific genes than those in wild-type iPSC-derived chondrocytes (FIG. 2).

Example 4

<Chondrocyte Proliferation and Extracellular Matrix Production>

In order to verify the cause of hyperplasia due to mutant-type iPSC-derived chondrocytes, analysis was conducted with a focus on the chondrocyte population doubling rate and the extracellular matrix production amount.

Figure 3:
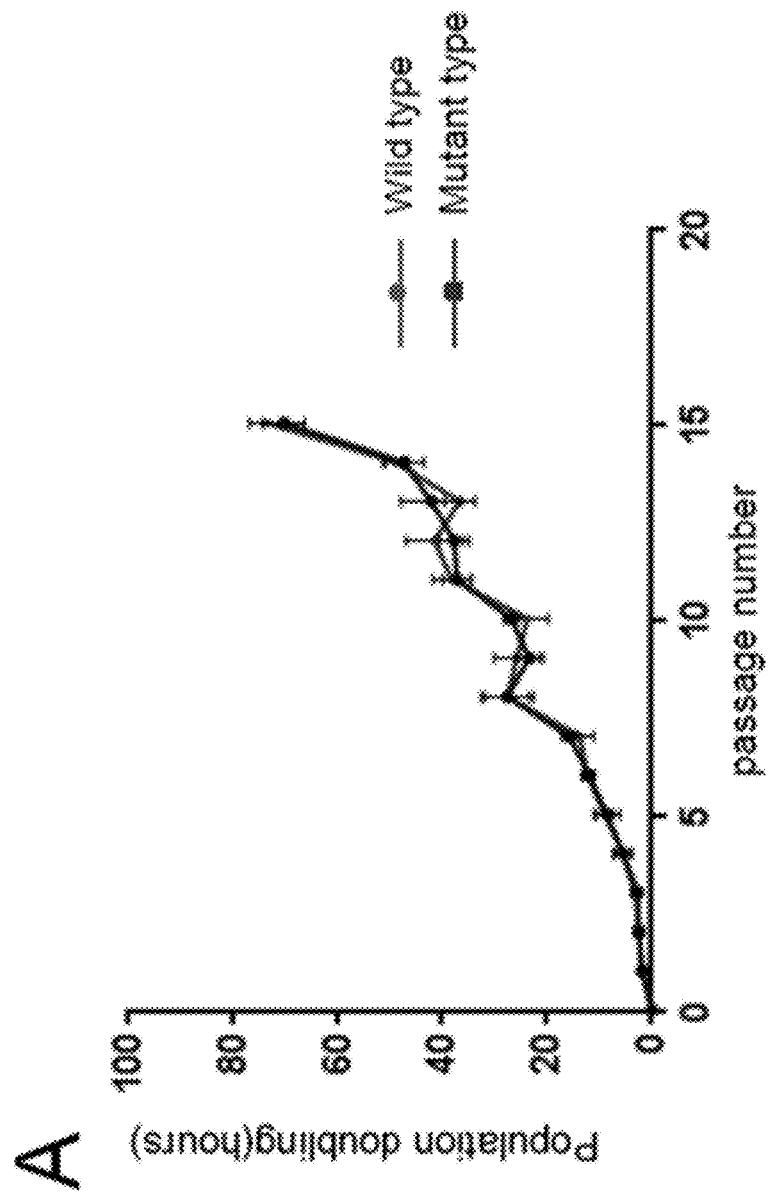
FIGS. 3A to 3C show results of examination of the cell population doubling rate of chondroprogenitor cells and the extracellular matrix production amount for wild-type iPSC- and mutant-type iPSC-derived cartilage tissues.
Figure 3:
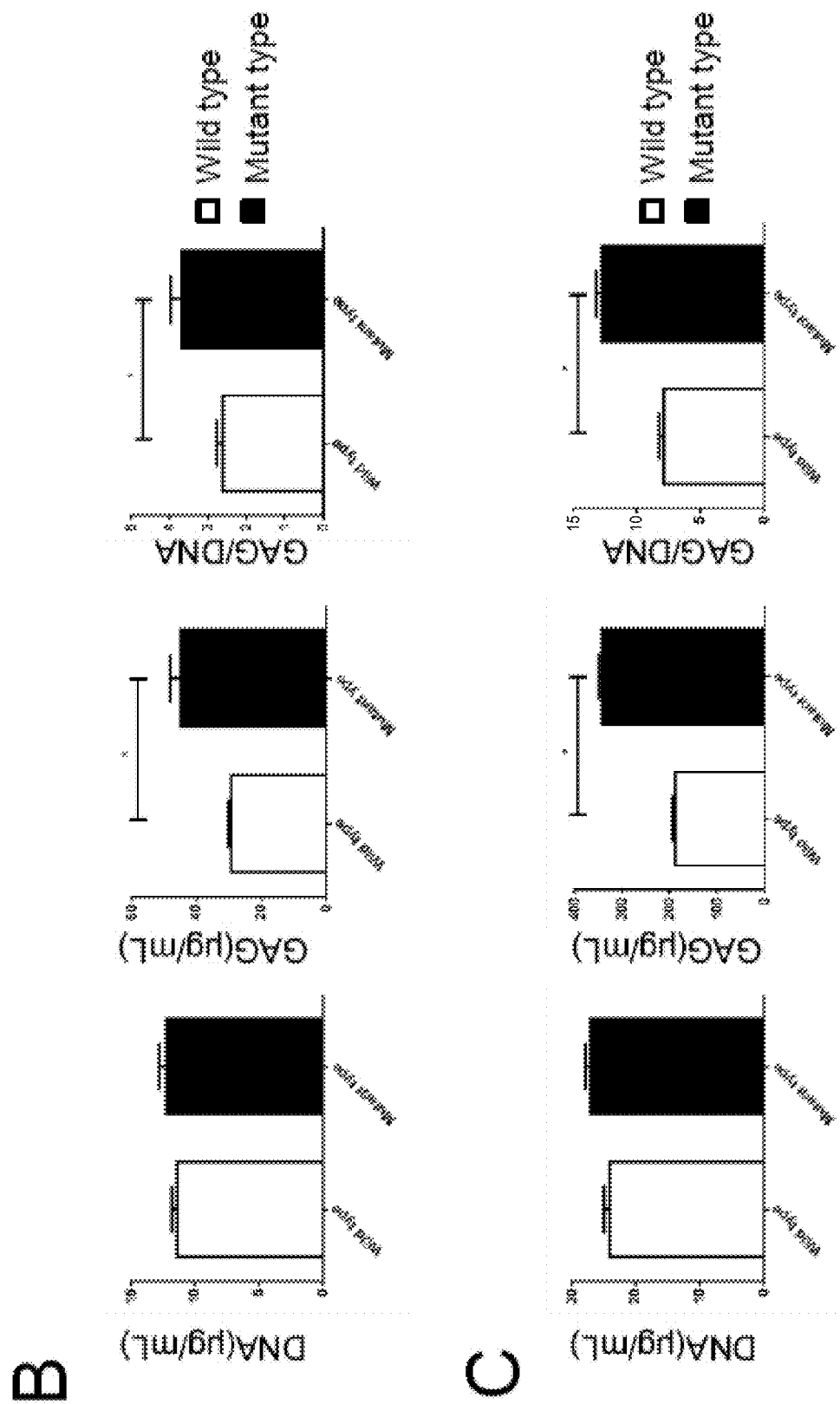

The chondroprogenitor cells obtained through differentiation induction in Example 2 were evaluated in terms of cell proliferation capacity during subculture with 15 passages. As a result, even though subculture with 15 passages was conducted at a frequency of one passage every three days, there was no difference in terms of cell proliferation between wild-type-derived and mutant-type-derived chondroprogenitor cells (FIG. 3A).

Subsequently, quantitative analysis of the amount of DNA and the glycosaminoglycan production amount after chondrocyte differentiation was conducted. The amount of DNA was determined using a Pico Green dsDNA Quantitation kit (Invitrogen) in the manner described in Nasu A, et al., PloS one. 8(1): e53771 (2013). The extracellular matrix production amount was determined using Blyscan glycosaminoglycan Assay (Biocolor) in accordance with the manufacturer's protocol. As a result, no difference in the amount of DNA in chondrocytes was found between wild-type iPSC-derived cartilage tissue and mutant-type iPSC-derived cartilage tissue in both cases of 2D micromass culture and 3D pellet culture (FIGS. 3B and 3C). This showed that a substantially equivalent number of chondrocytes are produced from wild-type iPS cells and mutant-type iPS cells. Meanwhile, it was observed that glycosaminoglycan, which is an extracellular matrix component, was produced in mutant-type iPSC-derived chondrocytes to a greater extent than that in wild-type iPSC-derived chondrocytes in both cases of 2D micromass culture and 3D pellet culture (FIGS. 3B and 3C). The increase of the cartilaginous extracellular matrix production amount, which was irrelevant to cell proliferation, was confirmed for mutant-type iPS cells based on the above results.

Example 5

<Increased Expression of SOX9>

Figure 4:
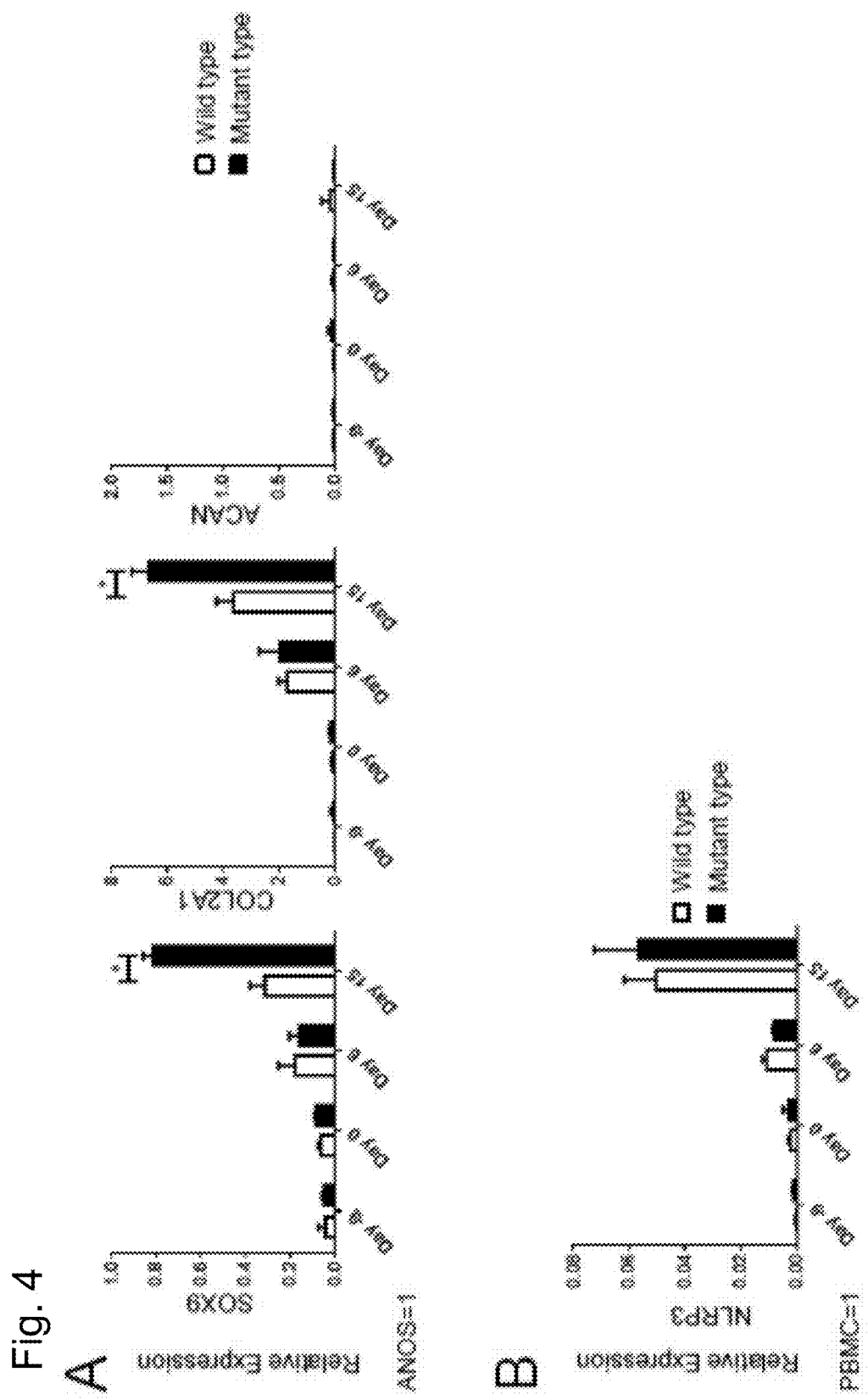
FIGS. 4A and 4B show the amounts of mRNA of chondrocyte-specific genes at the stage of induction of chondroprogenitor from wild-type iPS cells and mutant-type iPS cells (day −9 to day 15).

In order to examine the mechanism of excessive production of cartilaginous extracellular matrix described above, the expression levels of the respective chondrocyte-specific genes at the chondroprogenitor cell induction stage and the cartilage induction stage were examined (FIG. 2 and FIG. 4A). Among the chondrocyte-specific genes, SOX9 and COL2A1 were increasingly expressed in chondroprogenitor cells and chondrocytes that had been induced from mutant-type iPS cells on days 15 and 29 of induction, while ACAN and COMP were increasingly expressed in mutant-type iPSC-derived chondrocytes only on day 29. The results suggested that the expression of SOX9 probably contributes to triggering of the expression of other chondrocyte-specific genes. In addition, there was no significant difference in the amount of mRNA of NLRP3 depending on the presence or absence of mutations (FIG. 4B). Thus, the expression of SOX9 depended on the expression of mutant NLRP3 and the increased expression of SOX9 resulted in the expression of other chondrocyte-specific genes, suggesting that SOX9 contributes to excessive production of cartilaginous extracellular matrix.

Example 6

<In Vivo Chondrocyte Differentiation>

An implantation experiment was conducted to assess in vivo behaviors of a cartilaginous pellet obtained via differentiation induction of iPS cells from NOMID patients (mutant-type iPS cells). A cartilaginous pellet obtained on day 20 of 3D pellet culture (day 38 of differentiation induction) described above was wrapped with 0.5 cm×1 cm Gelfoam (Pfizer) and subcutaneously implanted in the dorsal regions of NOD/scid/γcnull mice. Four weeks later, cartilage tissue/bone particles were collected and fixed with paraformaldehyde for 24 hours, embedded in plastic, and cut to obtain 5-μm sections, followed by Hematoxylin and Eosin (HE), von Kossa, or Alcian Blue staining.

Figure 5:
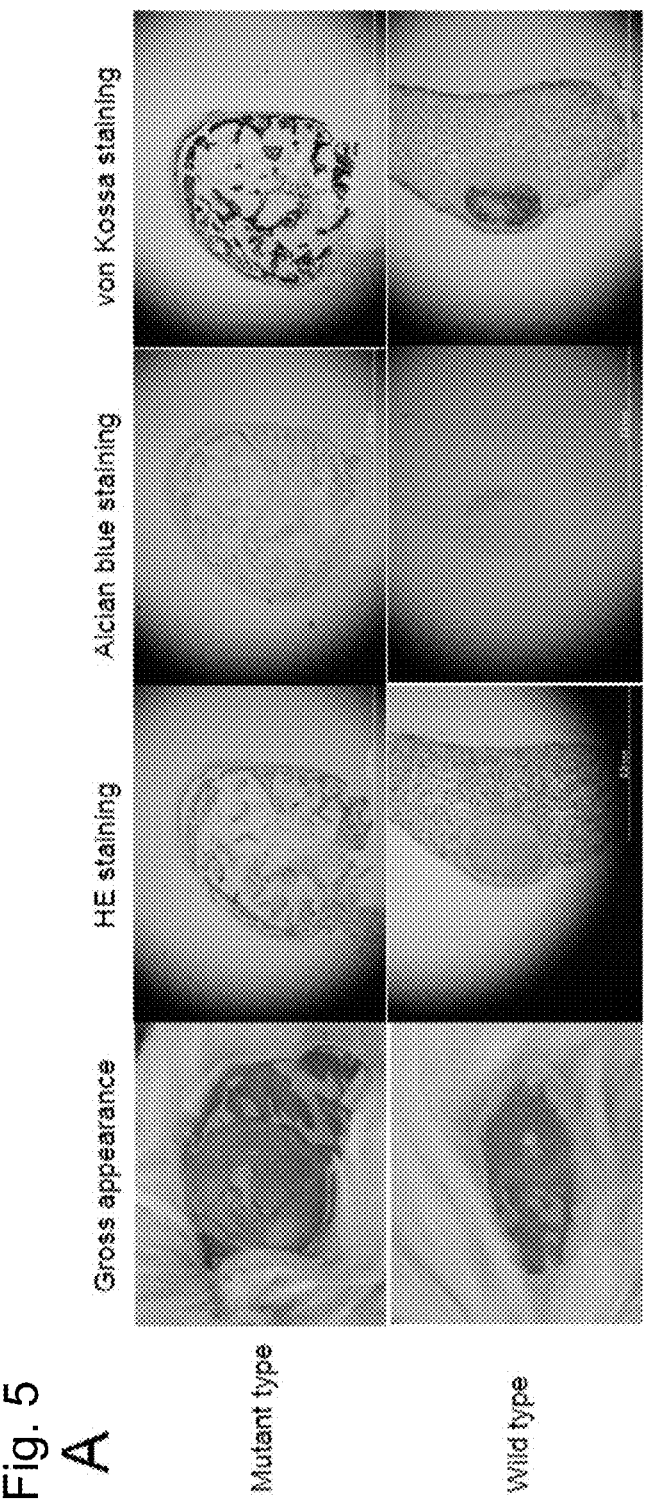
FIGS. 5A and 5B show results of in vivo maturation of cartilaginous pellets obtained through differentiation induction via 3D pellet culture.
Figure 5:
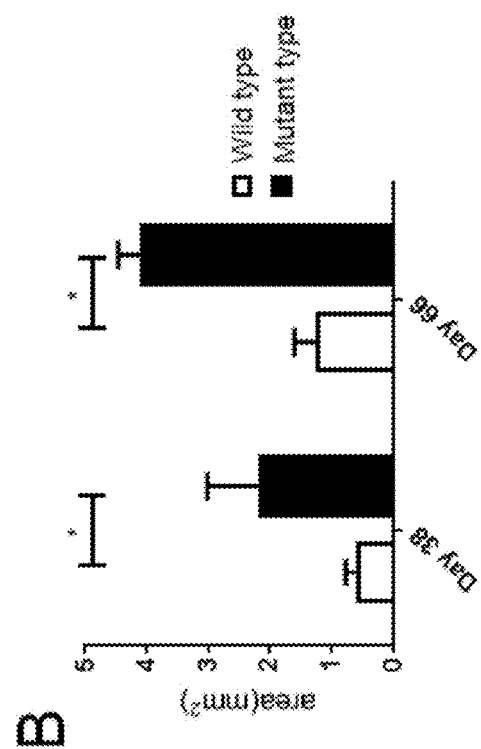

As a result, angiogenesis was confirmed in the implanted cartilaginous pellet (FIG. 5A). In addition, the size of the mutant-type iPSC-derived cartilaginous pellet was greater than that of the wild-type iPSC-derived cartilaginous pellet upon implantation and at the time of collection. The size difference increased in vivo (FIGS. 5A and 5B). As a result of von Kossa staining for detecting calcium deposition, calcification was observed in both the wild-type iPSC-derived cartilaginous pellet and the mutant-type iPSC-derived cartilaginous pellet (FIG. 5A). The results of Alcian blue staining revealed that the mutant-type iPSC-derived cartilaginous pellet contained cartilage components in amounts greater than those in the wild-type iPSC-derived cartilaginous pellet (FIG. 5A). Moreover, calcification in the mutant-type iPSC-derived cartilaginous pellet was nonuniform and unorganized, while calcification in the wild-type iPSC-derived cartilaginous pellet was uniform. Accordingly, the pathological conditions of joints of NOMID patients, such as hypertrophy and ectopic ossification, were reproduced as a result of the implantation of the mutant-type iPSC-derived cartilaginous pellet.

Example 7

<Influence of NLRP3 Inflammasome>

Figure 6:
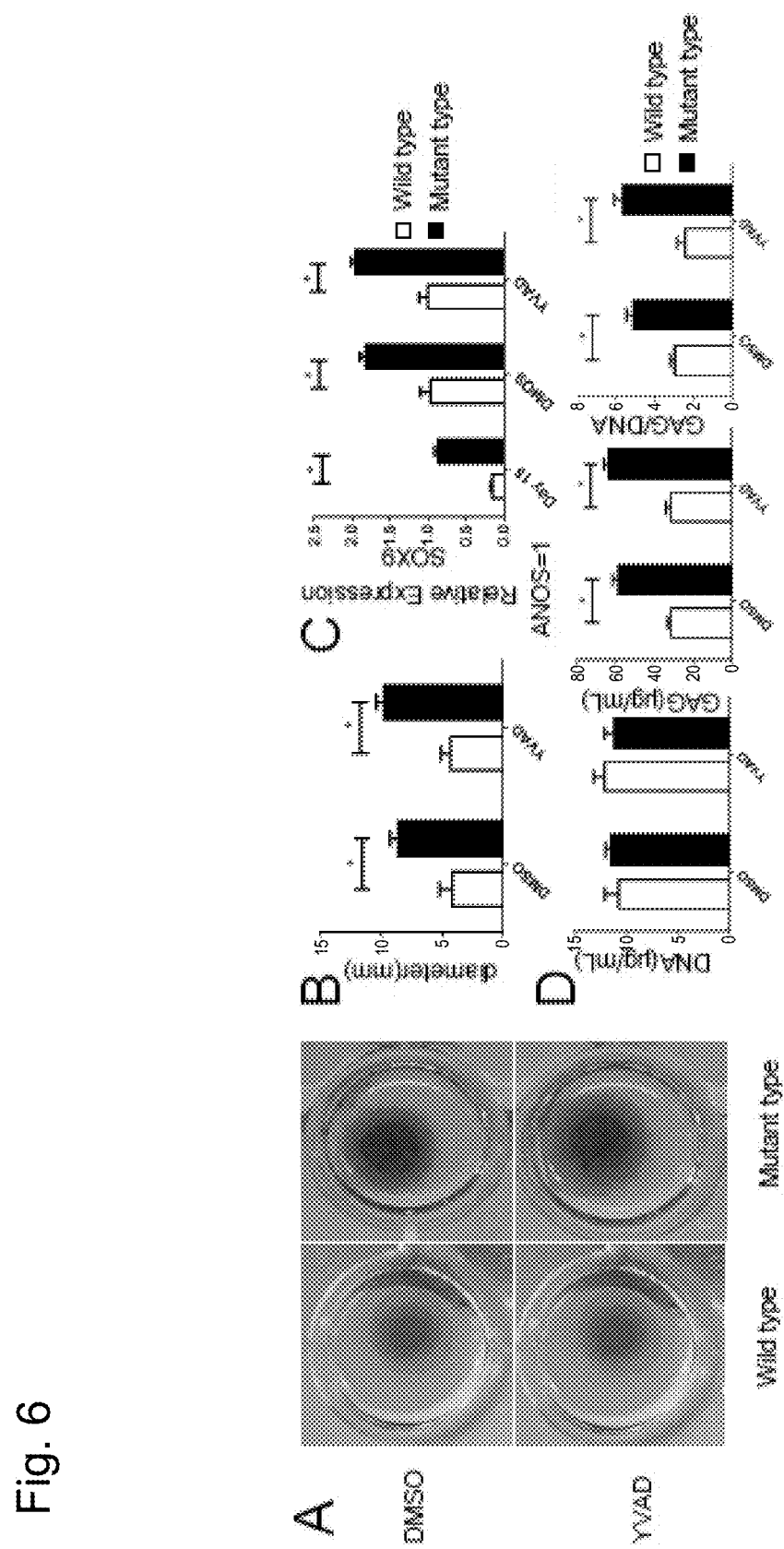
FIG. 6 shows analysis results for cartilage tissue obtained via culture with the addition of a caspase 1 inhibitor (Ac-YVAD) and an IL-1β inhibitor (IL1-Ra) upon chondrocyte induction.
Figure 6:
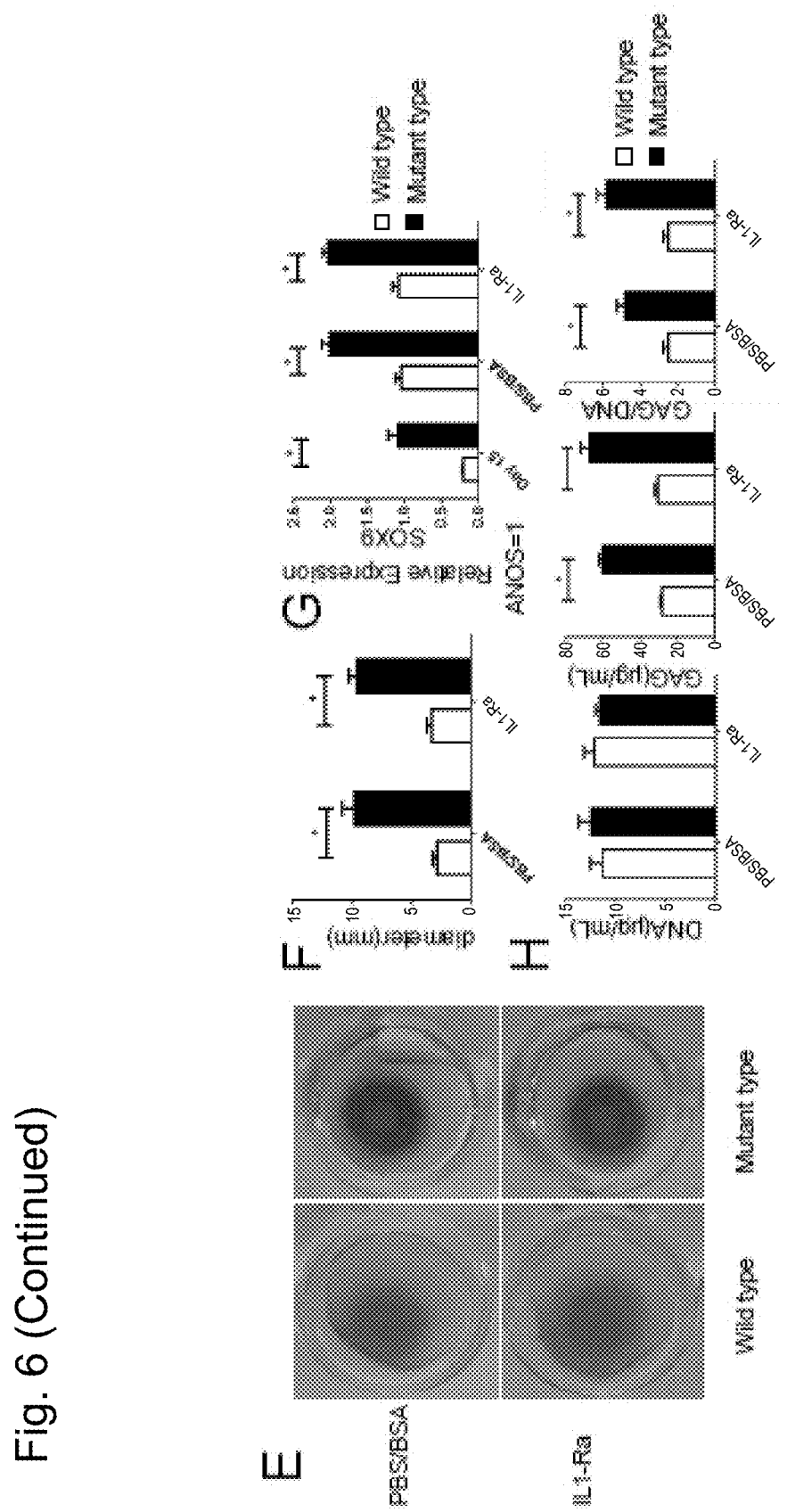

There was no change in caspase 1 activity or the IL-1β secretion amount for the aforementioned mutant-type iPSC-derived chondrocytes obtained via 2D micromass culture, indicating that the mechanism of excessive cartilaginous extracellular matrix production is independent of NLRP3 inflammasome. Further, 2D micromass culture was performed with the addition of 10 μM or 1 μg/mL Ac-YVAD-CHO. As a result, there was no influence in cartilaginous hyperplasia (FIGS. 6A, 6B, 6D, 6E, 6F, and 6H) or SOX9 expression (FIGS. 6C and 6G). The above suggested that it would be impossible to inhibit cartilaginous hyperplasia with drugs involved in inhibition of NLRP3 inflammasome.

Example 8

<SOX9 Promoter Activity and Identification of Downstream Factors>

Figure 7:
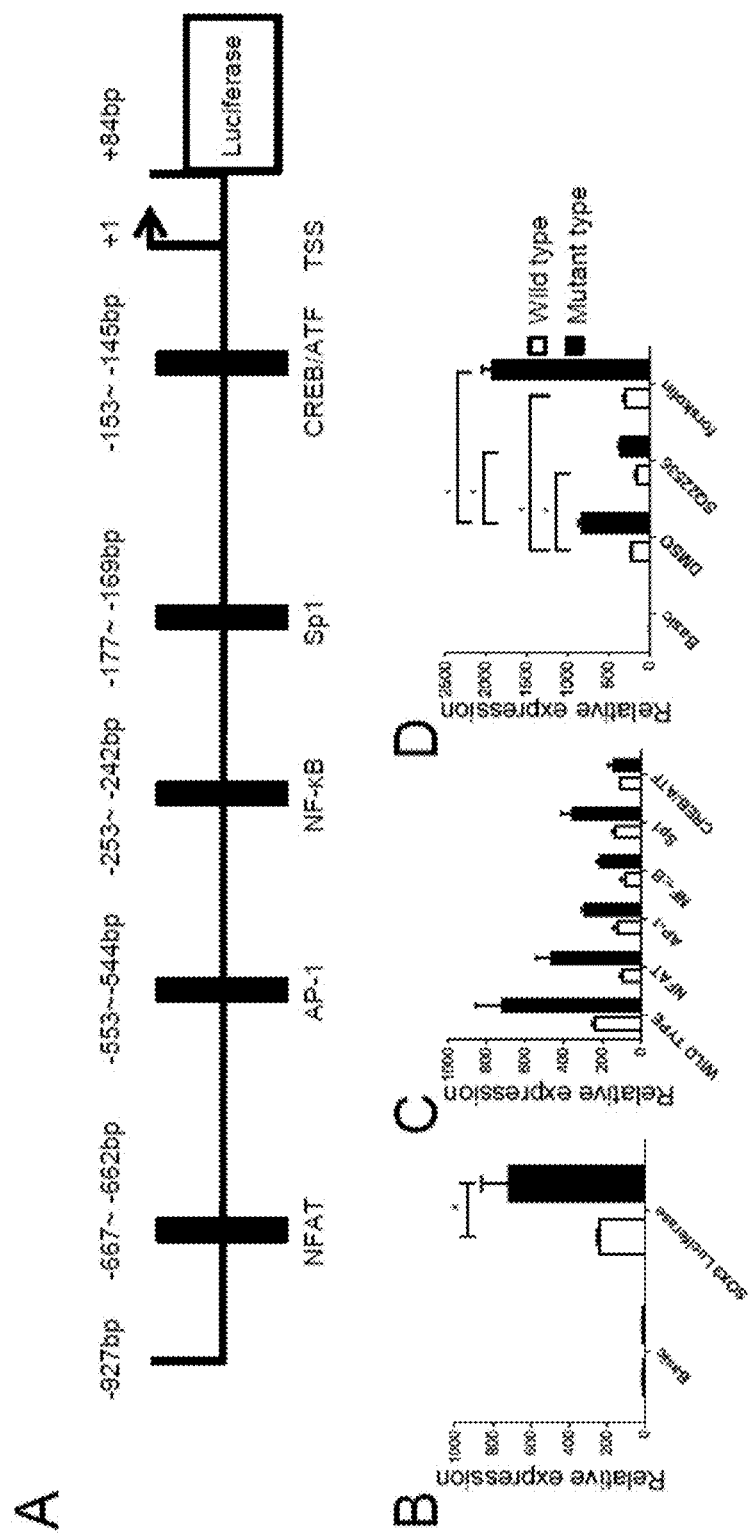
FIGS. 7A to 7D show analysis results of the mechanism of SOX9 overexpression in mutant-type chondrocytes. The results indicate that overexpression of SOX9 in mutant-type chondrocytes occurs in a manner dependent of the cAMP/PKA/CREB signal transduction pathway.
FIG. 7E shows results of determining the SOX9 expression level in wild-type chondroprogenitor cells and mutant-type chondroprogenitor cells to which forskolin and SQ22536 were added.
FIGS. 7F and 7G show Alcian Blue staining images and results of determining the stained area for cartilaginous pellets of wild-type chondrocytes and mutant-type chondrocytes induced via 3D culture to which forskolin and SQ22536 were added.
FIG. 7H shows results of determining the intracellular cAMP concentration for wild-type and mutant-type iPS cells (day 0) and chondroprogenitor cells (day 15).
FIG. 7I shows Western blotting analysis results of phosphorylated CREB (P-CREB) in mutant-type chondroprogenitor cells (MT1, MT2, and MT3) and wild-type chondroprogenitor cells (WT1, WT2, and WT3).
Figure 7:
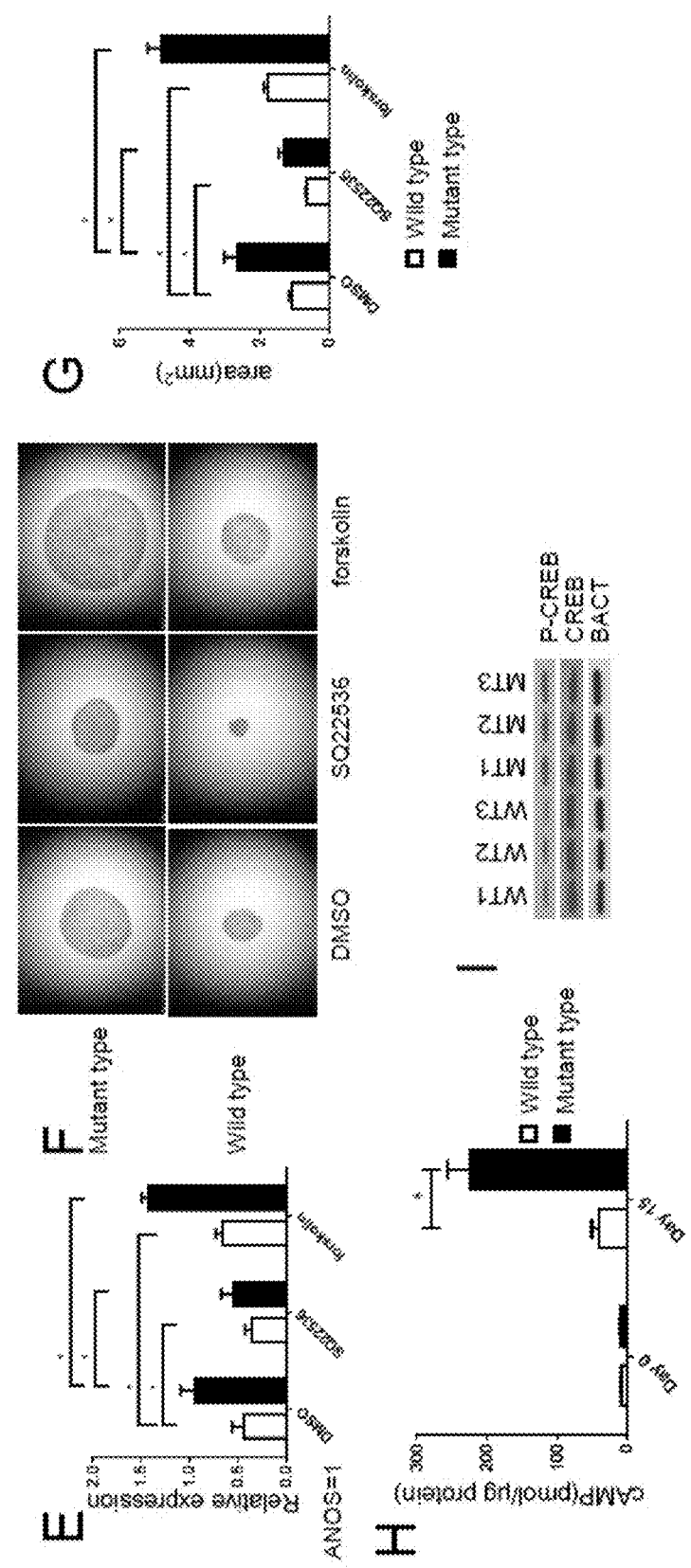

In order to examine SOX9 regulation, human SOX9 promoter activity in chondroprogenitor cells was confirmed. A reporter construct prepared by inserting a −927- to +84-bp human SOX9 promoter region (transcription start site: 0) into a pGL3-luciferase reporter plasmid (Promega) in accordance with Ushita M et al., Osteoarthritis and cartilage/ OARS, Osteoarthritis Research Society. 2009; 17(8): 1065-75 was used for confirmation (FIG. 7A and Table 2). Chondroprogenitor cells obtained by the above method were seeded on a 6-well plate (50000 cells/well). A FuGENE 6 transfection reagent was used for transfection (2 μg DNA/well). Twenty four hours later, luciferase activity was determined using a Dual-Luciferase Reporter Assay Kit (Promega) and a Centro XS³ LB 960 Microplate Luminometer (BERTHOLD) for calculation of promoter activity. As a result, the SOX9 promoter activity in mutant-type iPSC-derived chondroprogenitor cells was found to be higher than that in wild-type iPSC-derived chondroprogenitor cells (FIG. 7B). Next, in order to identify mutation of a site responsible for NLRP3-dependent responsiveness, reporter constructs each having a mutation in an NFAT-binding sequence, an AP-1-binding sequence, an NF-κB-binding sequence, an Sp1-binding sequence, or an CREB/ATF-binding sequence were prepared as listed in Table 3. These mutated reporter constructs were transfected into chondroprogenitor cells in the above manner to confirm promoter activity. As a result, no difference in promoter activity was found between mutant-type iPSC-derived chondroprogenitor cells and wild-type iPSC-derived chondroprogenitor cells in the case of a reporter having a mutation at the CREB/AFT binding site (FIG. 7C). The above results suggested that the CREB/ATF binding site is a transcription factor binding site that plays an important role in NLRP3-dependent SOX9 promoter activity.

TABLE 2

SOX9 promoter region (SEQ ID NO: 9)

CTCAAAGCCAGAGCAGTTAGCAAACTCTCCCCCAGACAGGGCGACTCG

GCTGACGTTTTTGACCCGGCCAGGAGGCAAAGACCAAAACGTCAGAGC

AGTAGCCCTGTTACTGAGGAGCGTCGGCAGGGTCGCGGGTAGAGGGGG

CTGGAGAATGACTTGTCAGAGCTCAAGGTCGATGTGGCGCGGGCGGC

CTCGAGAGCGCCGGGCTCCTGCGTGGCCACGGCCGCCGCTGCCAACCTT

CGCGGGGACTTAGCTTTGC<u>TTTCCA</u>TTGACTCCCTTTGCAAAAGCGCAG

CAGAATCCTGACCAGCCGCACCAGCCCCGGCGAACCCGAGCATGTTAAT

CTATTTATATGGATTATTACGGAGGAACAGCGGGCGT<u>TGAGTCA</u>CCAAAA

CATTTGCTTCAAAAGACTATTTCTAAGCACTTTTGCAGGCAGGCAGGCTC

GCTCCAGGCGCGTAAACTCGGCTACGCATTAAGAAGCGGCTGCTTTTCG

AATACTGCAAACTCCAGCTAAGTCCCCGGTGCCGCGGAGAGAGCAGTG

AAAAGAAATGTCGGAGGTGGGGGTAGATCCTAGTCTAGACACACACACT

TGCGCGCACACACACACACACACACACAAGATTCGCGCGGAGAAGGCA

CTAAAATTCTGGCATTCCGAGAGTACGACAAACTTACACACTT<u>GGAAGT</u>

<u>CCC</u>GGGTCCCCGCCTTCCCCGCAGCACCCCCGCCCCCCACCCTACC

GTCCGCCCTTTGGCTGCGAT<u>CCCCTCCCC</u>TCTCCTCCCCTCCCG<u>CCTCGT</u>

<u>CA</u>CCCAGCCCAGTGCCACAATCCTCCTCCCTCCCCAAAATCGGGTCCAA

TCAGCTGCCTGCCAACCCTGGGACTGCTGTGCTGTGATTGGCGGGTGGC

TCTAAGGTGAGGCGGAGTATTTATTAAAGAGACCCTGGGCTGGGAGTTG

GAGAGCCGAAAGCGGAGCTCGAAACTGACTGGAAACTTCAGTGGCGCG

GAGACTCGCCAGTTTCAACCCCGGAAACTTTTCT

※In the sequence, the NFAT-binding sequence, AP-1-binding sequence, NF-κB-binding sequence, Sp1-binding sequence, and CREB/ATF-binding sequence are underlined from the 5' side.

TABLE 3

| Transcription factor binding site | Wild-type sequence | Mutant-type sequence |
|---|---|---|
| NFAT | TTTTCCA (SEQ ID NO: 15) | Tagctag (SEQ ID NO: 10) |
| AP-1 | TGAGTCA (SEQ ID NO: 16) | Gcttctc (SEQ ID NO: 11) |
| NF-κB | GGGAAGTCCC (SEQ ID NO: 17) | GttAAGTCaa (SEQ ID NO: 12) |
| Sp1 | CCCCTCCCCC (SEQ ID NO: 18) | aaagagaggC (SEQ ID NO: 13) |
| CREB/ATF | CCTCGTCA (SEQ ID NO: 19) | Agttaggc (SEQ ID NO: 14) |

Example 9

<Recovery from Cartilaginous Hyperplasia with the Use of an Adenylate Cyclase Inhibitor>

In order to examine whether or not the AMP/PKA/CREB signal transduction pathway is involved in cartilaginous hyperplasia, analysis was conducted using forskolin, which is an adenylate cyclase activator, and SQ22536, which is an adenylate cyclase inhibitor. This test was conducted by introducing a human SOX9 promoter into chondroprogenitor cells, immediately treating the cells with 10 μM forskolin (CALBIOCHEM) or 10 μM SQ22536 (Sigma-Aldrich), and incubating cells for 24 hours so as to determine luciferase activity. As a result, the SOX9 promoter activity in mutant-type chondroprogenitor cells treated with forskolin increased to a level 2.3 times that of mutant-type chondroprogenitor cells (control) treated with a base (DMSO) (FIG. 7D). Meanwhile, the SOX9 promoter activity in mutant-type chondroprogenitor cells treated with SQ22536 decreased to a level half that in the control (FIG. 7D). Also, for wild-type chondroprogenitor cells, similar effects of forskolin and SQ22536 were observed (FIG. 7D). These data correlated with the effects of forskolin and SQ22536 on mRNA expression of SOX9 (FIG. 7E).

Further, the influence of adenylate cyclase was examined with the addition of forskolin and SQ22536 during 3D pellet culture. Accordingly, the sizes of mutant-type chondroprogenitor cells treated with forskolin increased to a level 2.0 times the sizes of mutant-type chondroprogenitor cells treated with a base (DMSO) (control) (FIGS. 7F and 7G). Meanwhile, the size of mutant-type chondroprogenitor cells treated with SQ22536 decreased to a level 2.1 times less than that of the control (FIGS. 7F and 7G). Also, for wild-type chondroprogenitor cells, similar effects of forskolin and SQ22536 were observed (FIGS. 7F and 7G). The above results suggested that adenylate cyclase activity of mutated NLRP3 causes the SOX9 expression to promote, and thus it is involved in cartilaginous hyperplasia. This indicated that it would be possible to suppress such cartilaginous hyperplasia by inhibiting adenylate cyclase.

Furthermore, the intracellular cAMP concentration was determined using a cAMP enzyme-linked immunoassay kit (Cell Signaling Technology, Inc.). As a result, the concentration in mutant-type iPSC-derived chondroprogenitor cells was found to be four times higher than that in wild-type iPSC-derived chondroprogenitor cells (FIG. 7H).

Next, in order to examine the state of phosphorylation of CREB located downstream of the AMP/PKA/CREB signal transduction pathway, Western blotting analysis was conducted as follows. Proteins were extracted using an M-PER Mammalian Protein Extraction Reagent (PIERCE) to prepare a cell lysate. Equivalent amounts of the proteins were added to Mini-PROTEAN TGX precast gels (Bio-Rad) and blotted on Immobilon PVDF membranes (Millipore). Each membrane was blocked and brought into contact with a different primary antibody, followed by incubation for 1 hour. Then, HRP-conjugated goat anti-mouse or anti-rabbit IgG (Santa Cruz) was added, followed by incubation for 1 hour. Each membrane was washed and subjected to detection with an ECL Advance Western blotting detection kit (GE Healthcare). Antibodies against CREB and phosphorylated CREB were purchased from Cell Signaling Technology, Inc.

As a result, also regarding CREB phosphorylation, which is induced when the AMP/PKA/CREB signal transduction pathway is activated, the degree of phosphorylation in mutant-type iPSC-derived chondroprogenitor cells was found to be higher than that in wild-type iPSC-derived chondroprogenitor cells (FIG. 7I).

The above indicated that the AMP/PKA/CREB signal transduction pathway plays an important role in the increase of SOX9 expression and causes hyperplasia of mutant-type cartilage tissue.

INDUSTRIAL APPLICABILITY

The present invention has been achieved based on the success in reproducing clinical conditions of cartilaginous hyperplasia by inducing iPS cells from somatic cells of cartilaginous hyperplasia patients to differentiate into chondrocytes to cause chondrogenesis. Therefore, the cells can be used for screening for a preventive and/or therapeutic drug for cartilaginous hyperplasia. Also, according to the present invention, a substance capable of suppressing differentiation into chondrocytes, which is obtained as a result of such screening, is provided. The substance can be used as a novel preventive and/or therapeutic drug for cartilaginous hyperplasia.

[Sequence Listing Free Text]

SEQ ID NOs: 1 to 8: Primers
SEQ ID NOs: 10 to 14: Mutant-type binding sites

All publications, patents, and patent applications cited herein are incorporated herein by reference in their entirety.

The invention claimed is:

1. A method of screening for a therapeutic and/or preventive drug for cartilaginous hyperplasia, comprising:
 (a) culturing chondroprogenitor cells derived from iPS cells having a NLRP3 mutation under conditions that induce cartilaginous hyperplasia in vitro;
 (b) growing a first population of chondroprogenitor cells which are brought into contact with a test substance and a second population of chondroprogenitor cells which are not brought into contact with the test substance;
 (c) detecting promoter activity of SOX9 in the cells obtained in step (b); and
 (d) determining that the test substance is a therapeutic drug and/or preventive drug for cartilaginous hyperplasia when the promoter activity of SOX9 is lower in the first population of chondroprogenitor cells compared to that observed in the second population of chondroprogenitor cells.

2. The method according to claim 1, further comprising quantifying the amount of SOX9 mRNA.

3. The method according to claim 1, wherein the NLRP3 mutation is a Tyr570Cys or Gly307Ser mutation in NLRP3.

4. The method according to claim 1, wherein cartilaginous hyperplasia is chronic infantile neurological cutaneous and articular syndrome.

* * * * *

SEQUENCE LISTING

<160> NUMBER OF SEQ ID NOS: 19

<210> SEQ ID NO 1
<211> LENGTH: 18
<212> TYPE: DNA
<213> ORGANISM: Artificial Sequence
<220> FEATURE:

<223> OTHER INFORMATION: primer

<400> SEQUENCE: 1
gacttccgcg acgtggac                                                  18

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
gttgggcggc aggtactg                                                  18

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
ggcaatagca ggttcacgta ca                                             22

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
cgataacagt cttgccccac tt                                             22

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
caactgtccc cagaagagca a                                              21

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
tggtagccaa agatgaagcc c                                              21

<210> SEQ ID NO 7
<211> LENGTH: 17
<212> TYPE: DNA
<213> ORGANISM: Artificial Sequence
<220> FEATURE:
<223> OTHER INFORMATION: primer

<400> SEQUENCE: 7
tcgaggacag cgaggcc                                                   17

```
<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
tcgagggtgt agcgtgtaga ga                                             22

<210> SEQ ID NO 9
<211> LENGTH: 1010
<212> TYPE: DNA
<213> ORGANISM: Homo sapiens

<400> SEQUENCE: 9
ctcaaagcca gagcagttag caaactctcc cccagacagg gcgactcggc tgacgttttt    60
gacccggcca ggaggcaaag accaaaacgt cagagcagta gccctgttac tgaggagcgt    120
cggcagggtc gcgggtagag ggggctggag aatgacttgt cagagctcaa ggtcgatgtg    180
gcgcggggcg gcctcgagag cgccgggctc ctgcgtggcc acggccgccg ctgccaacct    240
tcgcggggac ttagctttgc tttccattga ctccctttgc aaaagcgcag cagaatcctg    300
accagccgca ccagccccgg cgaacccgag catgttaatc tatttatatg gattattacg    360
gaggaacagc gggcgttgag tcaccaaaac atttgcttca aaagactatt tctaagcact    420
tttgcaggca ggcaggctcg ctccaggcgc gtaaactcgg ctacgcatta agaagcggct    480
gcttttcgaa tactgcaaac tccagctaag tccccggtgc cgcggagaga gcagtgaaaa    540
gaaatgtcgg aggtgggggt agatcctagt ctagacacac acacttgcgc gcacacacac    600
acacacacac acaagattcg cgcggagaag gcactaaaat tctggcattc cgagagtacg    660
acaaacttac acacttggaa gtcccgggtc ccccgccttc cccgcagcac cccccgcccc    720
cccaccctac cgtccgccct ttggctgcga tcccctcccc tctcctcccc tcccgcctcg    780
tcacccagcc cagtgccaca atcctcctcc ctccccaaaa tcgggtccaa tcagctgcct    840
gccaaccctg ggactgctgt gctgtgattg gcgggtggct ctaaggtgag gcggagtatt    900
tattaaagag accctgggct gggagttgga gagccgaaag cggagctcga aactgactgg    960
aaacttcagt ggcgcggaga ctcgccagtt tcaaccccgg aaacttttct               1010

<210> SEQ ID NO 10
<211> LENGTH: 7
<212> TYPE: DNA
<213> ORGANISM: Artificial Sequence
<220> FEATURE:
<223> OTHER INFORMATION: mutant binding site

<400> SEQUENCE: 10 tagctag                                                              7

<210> SEQ ID NO 11
<211> LENGTH: 7
<212> TYPE: DNA
<213> ORGANISM: Artificial Sequence
<220> FEATURE:
<223> OTHER INFORMATION: mutant binding site

<400> SEQUENCE: 11 gcttctc                                                              7

<210> SEQ ID NO 12
```

```
<211> LENGTH: 10
<212> TYPE: DNA
<213> ORGANISM: Artificial Sequence
<220> FEATURE:
<223> OTHER INFORMATION: mutant binding site

<400> SEQUENCE: 12
gttaagtcaa                                                              10

<210> SEQ ID NO 13
<211> LENGTH: 10
<212> TYPE: DNA
<213> ORGANISM: Artificial Sequence
<220> FEATURE:
<223> OTHER INFORMATION: mutant binding site

<400> SEQUENCE: 13
aaagagaggc                                                              10

<210> SEQ ID NO 14
<211> LENGTH: 8
<212> TYPE: DNA
<213> ORGANISM: Artificial Sequence
<220> FEATURE:
<223> OTHER INFORMATION: mutant binding site

<400> SEQUENCE: 14 agttaggc                                                                 8

<210> SEQ ID NO 15
<211> LENGTH: 7
<212> TYPE: DNA
<213> ORGANISM: Homo sapiens

<400> SEQUENCE: 15 ttttcca                                                                  7

<210> SEQ ID NO 16
<211> LENGTH: 7
<212> TYPE: DNA
<213> ORGANISM: Homo sapiens

<400> SEQUENCE: 16 tgagtca                                                                  7

<210> SEQ ID NO 17
<211> LENGTH: 10
<212> TYPE: DNA
<213> ORGANISM: Homo sapiens

<400> SEQUENCE: 17
gggaagtccc                                                              10

<210> SEQ ID NO 18
<211> LENGTH: 10
<212> TYPE: DNA
<213> ORGANISM: Homo sapiens

<400> SEQUENCE: 18
cccctccccc                                                              10

<210> SEQ ID NO 19
<211> LENGTH: 8
<212> TYPE: DNA
<213> ORGANISM: Homo sapiens
```

```
<400> SEQUENCE: 19 cctcgtca                                                                    8
```